(12) United States Patent
Shlezinger et al.

(10) Patent No.: US 7,800,741 B2
(45) Date of Patent: Sep. 21, 2010

(54) METHOD FOR EVALUATION OF A GEMSTONE

(75) Inventors: Haim Shlezinger, Tel Aviv (IL); Ran Ziskind, Rosh Pina (IL); Gabi Horowitz, Doar-Na Misgav (IL); Michael Eroshov, Nahariya (IL); Adam Devir, Haifa (IL); Dan Sheffer, Doar-Na Misgav (IL)

(73) Assignee: Galatea Ltd., Rosh Pina (IL)

( * ) Notice: Subject to any disclaimer, the term of this patent is extended or adjusted under 35 U.S.C. 154(b) by 281 days.

(21) Appl. No.: 12/071,524

(22) Filed: Feb. 21, 2008

(65) Prior Publication Data

US 2008/0231833 A1 Sep. 25, 2008

Related U.S. Application Data

(63) Continuation-in-part of application No. PCT/IB2006/052884, filed on Aug. 21, 2006.

(30) Foreign Application Priority Data

Aug. 22, 2005 (DE) ......................... 10 2005 039 679
Feb. 21, 2007 (IL) ....................................... 181484

(51) Int. Cl.
*G01N 21/87* (2006.01)
*G01N 21/88* (2006.01)
(52) U.S. Cl. ......................... 356/30; 356/73; 356/239.1
(58) Field of Classification Search .................. 356/30, 356/36
See application file for complete search history.

(56) References Cited

U.S. PATENT DOCUMENTS 2,494,078 A * 1/1950 Woodruff ..................... 356/30

(Continued)

FOREIGN PATENT DOCUMENTS

BE 1013663 5/2002

(Continued)

OTHER PUBLICATIONS

Meyrowitz, R. "A Compilation and Classification of Immersion Media of High Index of Refraction"; U.S. Geological Survey, Washington 25, D.C.; pp. 398-409.

(Continued)

*Primary Examiner*—F. L Evans
(74) *Attorney, Agent, or Firm*—The Nath Law Group; Derek Richmond; Robert T. Burns

(57) ABSTRACT

An apparatus for determining location of at least one inclusion in a gemstone having a first refractive index, comprising:
  a container adapted for containing a material having a second refractive index,
  a holder operative to support a gemstone in the material when the container contains the material;
  an illuminator positioned and adapted to illuminate said gemstone when disposed within said material in said container, with illumination at which said gemstone and said material have their respective first and second indices;
  a detector that detects illumination from the illuminated gemstone and said material and produces signals responsive thereto;
  a controller that receives the signals and is operative to determine a location of an inclusion in the gemstone based on the signals; and
  a system, operative to reduce the presence within said material, at least when the gemstone is disposed therein, of any substance other than inclusions, having a third refractive index.

69 Claims, 11 Drawing Sheets

U.S. PATENT DOCUMENTS

| | | | | |
|---|---|---|---|---|
| 2,627,276 | A | * | 2/1953 | Eggleton .................... 134/143 |
| 2,869,417 | A | | 1/1959 | Allen |
| 3,437,402 | A | | 4/1969 | Allen |
| 3,867,032 | A | | 2/1975 | Bruck |
| 4,049,350 | A | | 9/1977 | Brück |
| 4,112,955 | A | * | 9/1978 | Gollel ....................... 134/57 R |
| 4,152,069 | A | | 5/1979 | Bruck |
| 4,259,011 | A | | 3/1981 | Crumm et al. |
| 4,394,580 | A | | 7/1983 | Gielisse |
| 4,521,073 | A | | 6/1985 | Murakami et al. |
| 5,242,203 | A | * | 9/1993 | Agnew et al. .............. 294/99.2 |
| 5,253,103 | A | | 10/1993 | Boyd et al. |
| 5,379,102 | A | | 1/1995 | Takeuchi |
| 5,515,157 | A | * | 5/1996 | Can ............................ 356/30 |
| 5,905,584 | A | | 5/1999 | Osugi |
| 5,966,673 | A | | 10/1999 | Shannon, Sr. |
| 6,014,208 | A | | 1/2000 | Welbourn et al. |
| 6,020,954 | A | | 2/2000 | Aggarwal |
| 6,239,867 | B1 | | 5/2001 | Aggarwal |
| 6,473,164 | B1 | | 10/2002 | De Jong et al. |
| 6,813,007 | B2 | | 11/2004 | Lapa et al. |
| 7,001,038 | B2 | | 2/2006 | Bock et al. |
| 7,324,188 | B1 | | 1/2008 | Beesley |
| 2002/0030039 | A1 | | 3/2002 | Kerner |
| 2002/0052170 | A1 | | 5/2002 | Holloway |
| 2003/0107722 | A1 | | 6/2003 | Klingler |
| 2003/0223054 | A1 | | 12/2003 | Warwick |
| 2004/0051861 | A1 | | 3/2004 | Bray |
| 2004/0141320 | A1 | | 7/2004 | Bock et al. |
| 2005/0036132 | A1 | | 2/2005 | Lapa et al. |

FOREIGN PATENT DOCUMENTS

| | | |
|---|---|---|
| EP | 1158293 | 11/2001 |
| EP | 1211503 | 6/2002 |
| EP | 1630549 | 3/2006 |
| JP | 60-262036 | 12/1985 |
| RU | 2 035 039 C1 | 5/1995 |
| RU | 2 054 656 C1 | 2/1996 |
| WO | WO 83/00389 | 2/1983 |
| WO | WO 89/05280 | 6/1989 |
| WO | WO 89/12816 | 12/1989 |
| WO | WO 94/00399 | 1/1994 |
| WO | WO 96/04409 | 6/1996 |
| WO | WO 97/04302 | 2/1997 |
| WO | WO 99/61890 | 12/1999 |
| WO | WO 02/31474 | 4/2002 |
| WO | WO 02/46725 | 6/2002 |
| WO | WO 03/099054 | 12/2003 |
| WO | WO 03/103434 | 12/2003 |
| WO | WO 2005/052540 | 6/2005 |
| WO | WO 2007/023444 | 3/2007 |

OTHER PUBLICATIONS

Meyrowitz, R., et al. "Immersion Liquids of High Refractive Index"; pp. 746-750.

Tatarsky—"Crystal Optics and the Immersion Method of Mineral Assaying"; permitted by the USSR Ministry of Higher and Vocational Secondary Education; 1965; pp. 213-215; Nedra Publishing House, Moscow.

Anderson B., B. W. "Gem Testing"; 1988; Moscow "MIR"; Butterworths.

Diaexpert Brochure.

Deetlefs et al. "Neoteric Optical Media for Refractive Index Determination of Gems and Minerals", New Journal of Chemistry [Online], 30: 317-326, 2006. p. 317, col. 1, Line 12—p. 318, col. 1, Line 2, p. 324, col. 2—p. 326, col. 1, Figs.1, 5-8.

Larsen Jr. et al. "Measurement of the Refractive Index", Interantional Tables for Crystallography, XP009101445, C(Chap.3.3): 144, 2004. § [3.3.2].

McCormick "Advanced and Refined Technique in the Petrographic Study of Crystalline Refractories", Journal of the American Ceramic Society, XP009101414, 19(1-2): 7-13, Jan. 1936. p. 7, col. 2—p. 9, Coll, Line 5, Fig.1, Tables I, III.

Saker "The Optical Properties of Liquid Selenium", Proceedings of the Physical Society, Section B, 65: 785-787, 1952. Fig.3.

West "Immersion Liquids of High Refractive Index", The American Mineralogist [Online], XP002484248, 21: 245-249, 1936. Retrieved From the Internet: URL:http://www.minsocam.org/ammin/AM21/AM21_245.pdf>.

* cited by examiner

METHOD FOR EVALUATION OF A GEMSTONE

RELATED APPLICATIONS

This application claims priority from Israel Patent Application No. 181484 filed on Feb. 21, 2007, the content of which is incorporated by reference as if fully set forth herein.

This application is also a continuation-in-part (CIP) of PCT Patent Application No. PCT/IB2006/052884 filed on Aug. 21, 2006 and published as WO2007/023444, which claims priority from German Patent Application No. 10 2005 039 679.8 filed on Aug. 22, 2005. The content of these applications are incorporated by reference as if fully set forth herein.

FIELD OF THE INVENTION

The present invention relates to the determination of the properties of gemstones. In particular, the present invention relates to but not limited to location and properties of internal flaws and optionally on their effects on a rough stone and polished stone value.

BACKGROUND OF THE INVENTION

The terms 'gem', 'gemstone' and 'stone' are used interchangeably with the usual meaning referring to minerals such as diamonds, sapphires, rubies, emeralds and so on. In particular cases, without compromising generality, diamonds will be used to describe the invention.

The terms 'inclusion', 'flaw' and 'defect' are used interchangeably indicating an individual visually discernable irregularity inside the gem.

The term 'dividing plane' relates to planes through which a stone is sawed, cleaved or cut by any method into separate parts.

Gemstones, as ornamental objects rather than for industrial use, are valued by their appearance. In gemology, the quality of a gem such as a diamond, is typically determined by the "4C's", Clarity (internal perfection of the stone), Color (colorless being the more expensive), Cut (consisting of shape, proportions, symmetry, and polish), and Carat (weight).

As for clarity, it is desirable to identify the location and size of flaws inside a rough stone in order to determine the preferred dividing planes that would yield the greatest value from a given stone. Likewise it may be desirable to identify flaws in a polished stone in order to determine its value.

In everyday practice a stone is visually examined by experts who try to assess the location and size of the flaws using their experience and following industry rules. Still, it is a human subjective judgment that depends on a particular person's skill and experience and may vary between different individuals and circumstances. Moreover, when a parcel of gemstones is to be evaluated, it could take a long time to assess each stone, so that the parcel value is deduced upon the examination of representative stones only. In uncut gems, it is often virtually impossible to see, much less locate, internal flaws.

To overcome the manual inconsistency and the labor involved, optical methods and devices have been proposed for the detection of flaws in stones. However, the high refractive index of gems, especially diamonds, causes large refractions of incoming and outgoing light and total internal reflections resulting in multiple deflected images of the flaws.

U.S. Pat. No. 4,259,011 describes how to identify the presence of inclusions but not their location. European patent 1,211,503, presents a possible solution for the locating of inclusions in a transparent and at least partially polished diamond by imaging the diamond twice and analyzing the images by computer so as to localize an inclusion with respect to the outer surface of the diamond. Although this patent makes reference to a refractive index correction factor to be included in the computer's calculations, it does not provide a solution to multiple images produced by a single inclusion.

U.S. Pat. No. 4,049,350 teaches eliminating the refractions and reflections at the facets of a cut stone by submerging the stone in a solution of similar refraction index. It describes how to locate an inclusion in a two dimensional plane by aiming a narrow laser beam at a preferred angle to a particular facet.

U.S. Pat. No. 4,152,069 also teaches submerging a cut stone in such a solution and how to find the inclusion within a three dimensional volume.

Neither of the latter references discloses any information as to the medium they used to closely match the refraction index of the gem, this being particularly problematic for diamonds that have a very high refraction index. As far as is known to the present inventors, no such liquid has been suggested in the art for determining flaws in diamonds.

A paper entitled "The Optical Properties of Liquid Selenium" (E. W. Saker, Proc. Phys. Soc. 1952, pp. 785-787) provides some experimental results, including the refraction index of solid and molten selenium in the near infrared region with respect to temperature and wavelength. There is no suggestion in this paper of using this information in any way that is relevant to the problem of determining inclusions in diamonds.

U.S. Pat. No. 4,521,073 teaches an infrared light transmitting fiber produced by a process comprising preparing a core crystalline fiber having a high melting point and a high refractive index, forming around the core fiber a continuous layer of cladding crystal having a low melting point and a low refractive index, and subsequently forming a protective layer on the resulting step-index fiber. The patent teaches the use of Thallium iodide-bromide as the crystal, however, there is no suggestion in the patent of using this information in any way that is relevant to the problem of determining inclusions in diamonds.

Meyrowitz R. teaches materials and compounds having high refractive index in two publications, "Immersion Liquids of High refractive Index", 99. 746-750 and "A Compilation and Classification of Immersion Media of High Index of Refraction", pp. 398-409.

The disclosures of all of the above cited references are incorporated herein by reference.

SUMMARY OF THE INVENTION

An aspect of some embodiments of the invention relates to a method and apparatus for substantially reliable finding of the positions of inclusions within the structure of a gemstone which may be even a rough irregular or uncut stone.

An aspect of some embodiments of the invention relates to a method and apparatus for evaluating a gemstone with respect to its potential for producing polished gems responsive to the position and size of flaws relative to the external surfaces of a stone. Optionally, the color of the stone is also taken into consideration for evaluation of the gemstone. Optionally, the gemstone is a rough stone and is evaluated in terms of costs and value of potential polishing of the gem. Alternatively, the gemstone is a polished stone and is evaluated in terms of costs and value of the polished gem.

An aspect of some embodiments of the invention relates to a method and apparatus for deciding on the sawing planes in a gemstone to increase its potential value responsive to the position and size of flaws in the rough stone.

In an embodiment of the invention, the position of the inclusion with respect to the outside geometry is determined. Optionally, this information is used to determine possible sawing planes and/or an optimal set of sawing planes for the stone (optimal with respect to resultant gems). Alternatively, the internal stresses in the stone are taken in consideration when the sawing plane is defined. Alternatively or additionally a value of the rough stone and/or cut and polished gemstones that can be derived from the rough stone is determined.

Exemplary embodiments of methods according to various embodiments of the invention involve three actions: (a) determining the external structure of the stone, (b) locating the inclusions and determining their geometry, and (c) relating the positions of the inclusions to the external structure of the stone. Optionally, prior to (b), the surface of the stone is treated to clean the stone surface from possible foreign substances.

In an embodiment of the invention, an optical probe, comprising a light source and a sensor, is used to scan the stone and detect its external structure. In order to capture the structure of the stone from various points of view, the stone is optionally rotated relative to the probe. Alternatively, the probe is moved around the stone. The optical probe is, optionally, a commercially available device using one or more of the following techniques: Triangulation, Circumferential Triangulation, Structured light and Achromatic Confocal or Conoscopic Holography. The probe may be a spot probe (the probe measures one point at a time), a line probe (the probe illuminates a line on the object and measures along this line) or an area probe (the probe illuminates an area on the object and measure the whole area at a time).

Optionally, when a spot probe is used, the outcome received from a scan is a point cloud that is then interpolated to define a surface description of the stone. Optionally, the resolution of the scanning is 30 microns, the measuring spot is 8 microns and the accuracy is 1 micron.

Optionally, the external surface of the stone is scanned and continuous information is received and no interpolation is required.

In an exemplary embodiment of the invention, two or more of the above described scanning processes are performed at different positions of the stone, in order to scan all facets of the stone (or the sides of an uncut stone). In this embodiment, the results from the different processes are merged, to receive the external structure of the stone using "best fit" method. Other methods of determining the external structure of the gemstone, as known in the art, can be used, for example a mechanical probe, or laser probe.

The coordinates and datum of the external inspection setup are marked and/or preserved for correlation with the results of the internal examination. Optionally, before internal examination, a second external reference scan is performed in order to correlate the position of the stone with the external structure received from the first external scan process.

Optionally and additionally, internal stresses in the stone are detected and recorded using tools of the art, such as a polarizing apparatus.

In an embodiment of the invention, the gem is immersed in a medium having a refractive index substantially comparable to that of the gem, at least for a particular wavelength band of light and temperature. Thus, the refractions and internal reflections and multiple deflected images of inclusions are substantially eliminated. Light incident on the stone will largely pass through it, but an inclusion will absorb or reflect the light so that viewing the stone from a particular direction will produce an image with a dark region relative to a bright background, with the inclusion being on that line of sight (i.e. not substantially deflected).

Optionally and preferably, the medium has a low enough viscosity and surface tension to allow the material to enclose the stone. Material with such viscosity and surface tension will enable looking into a "Frosty" stone (a stone with a rough external surface that looks milky to the naked eye or when using conventional optic tools).

As the refraction index of any material is dependent on the light wavelength and the temperature, these parameters should be controlled in order to achieve a close match between the refraction index of the stone and the medium; that is, the stone and the immersing medium should be kept at a suitable temperature and the light filtered (or have a narrow intrinsic bandwidth) to allow only the appropriate wavelengths to reach the detector.

As a non-limiting preference, the medium should be substantially non-toxic and safe for industrial use.

Optionally said medium comprises at least one chalcogenide element in group 16 of the periodic table, such as sulphur, selenium or tellurium.

Preferably for an index of refraction close to that of a diamond, the medium comprises selenium; optionally selenium comprises a significant part of the medium. Optionally selenium comprises elemental selenium. In some embodiments of the invention the selenium is molten and the diamond is imaged with infrared or near-infrared light. Alternatively, the gemstone is immersed in the molten medium which subsequently solidifies, encasing the gemstone in a solid phase. Preferably, the solid selenium is in an amorphous form. Alternatively, the material is provided as part of a gel or high concentration dispersion or solution.

Optionally, the medium comprises a sulfur-based immersion medium containing one or more components such as selenium, arsenic, tellurium, arsenic disulfide, mercuric iodide, arsenic trisulfide, arsenous acid, bromine, iodine and combinations thereof. Optionally, the medium comprises thallium iodide-bromide. Optionally the medium may contain other ingredients to improve desired characteristics.

In an exemplary embodiment of the invention, contamination is prevented by treating the stone and/or its surroundings before immersing the stone in the immersion medium. Optionally, the stone is first cleaned with a cleaning medium and then washed with purified water. Optionally, the stone is then dried to remove moisture from the surface of the stone. Alternatively or additionally, vacuum or inert gas is applied in order to remove foreign substances from the surface of the stone and its surroundings.

In an exemplary embodiment of the invention, the stone is clamped or glued on a holder (dop or base) when treated for prevention of contamination. Optionally, two or more stones are treated in a single cleaning process, for example ten stones.

In an embodiment of the invention, the stone is fixed on a rotatable base and immersed in the medium. The stone is in a known position and rotation with respect to the setup coordinates. Optionally, the stone is kept on the base used for the external scanning and cleaning of the stone, such that the position of the stone is known with respect to a reference of the base. Optionally, the base is marked such that the position of the stone with respect to the external scan is known.

A light source illuminates the stone, and a suitable detector records its image for various orientations. The recorded image will comprise a distinctive impression of any detectable inclusion in the stone. The gem is imaged at a multiplicity of orientations as required for determination of the location of inclusions and/or a reconstruction of the inclusions position in the setup coordinates from the recorded images. In some embodiments of the invention, the reconstruction is a tomographic reconstruction. In others simple or redundant triangulation is used to determine the position of the inclusions. In some embodiments determination of the number and/or size of the inclusions in a single planar image suffices.

If the match in optical properties between the gemstone and the surrounding medium is perfect, then the inclusions will be imaged in correlation with their position from the outline of the stone (without deflection). If the match is not perfect there may be a "ghost" image of the inclusion, the distance between the "ghost" image and the "true" image is dependent on the difference between the refractive index of the stone and the medium, geometry of the stone, the distance of the inclusion from the surface of the stone and the orientation of the stone relative to the detector. Optionally, the dependency between the distances is a linear dependency. In some situations it may be possible to eliminate separate determination of the external structure and determine that structure and the relationship between the position of the inclusion and the external structure from a single set of images.

In an embodiment of the invention the setup coordinates used in the gem reconstruction of the external surface of the gem are matched with the coordinates of the setup used for the inclusion detection, optionally the same setup is used for both. Optionally, the gem is mounted on a same base for both inclusion mapping and external surface mapping. Having a model of the external structure of the gem and the positions of inclusions in matched or common setup coordinates, the inclusions' positions are mapped into the gem structure; alternatively or additionally, they are incorporated into the gem geometrical model.

In an embodiment of the invention the external geometry of the gemstone and the respective positions of the inclusions therein (both with respect to the setup coordinates) are combined to determine the position of the inclusions in the gemstone.

Optionally the positions of the inclusions are used to calculate dividing, e.g., sawing, planes to produce preferred polished gems. Optionally, the value of the polished gemstones is used to compute a preferred sawing plane or set of sawing planes. Optionally a value of the gemstone is established based on the value of the potential polished stones.

Optionally the preferred goal is largest flawless polished gems, so that the planes go through inclusion or isolating them.

Optionally the preferred goal is the highest value flawless polished gems such as better cut or shape at the expense of size whereby the planes go through inclusion or isolating them.

Alternatively, the preferred goal is highest value polished gems, some of which optionally including flaws, for example larger size or better cut on the expense of clarity;

Alternatively or additionally, the preferred goal is the better effectiveness of value to cost such as value less cost, or value per cost ratio.

Optionally, the algorithm may be tuned to use a combination of criteria for preferred value goals.

Optionally or additionally, the algorithm reports, for a stone, a set of preferred planes according to the specified goal or goals. Alternatively or additionally, it reports a list of sets of planes ranked according to the preferred goal or goals.

Alternatively or additionally, for a set of sawing planes of a stone the algorithm reports selected ones of the value of potential value of resultant polished gems, the cost involved, a value of cost effectiveness such as the value after cost deduction, and/or any other suitable value to cost relation.

Optionally or additionally, said report comprises the maximum net and/or gross (before cost) stone value.

Optionally, the stone model and respective sawing planes are recorded, and optionally reported, such that they can be read and construed for later use.

Optionally, any of the output of the aforementioned exemplary embodiments, namely, the stone structure, inclusions positions therein and preferred sawing planes, may be input into sawing and polishing machinery, optionally automatically.

Optionally, a photo of the texture of the stone is taken in order to project a 3D model of the stone with the inclusions.

In an embodiment of the invention, marks are made on the external surface of the stone to enable alignment of the stone for sawing. In an embodiment of the invention, the marks are made while the stone is in the set-up. Optionally, the marks are made by a laser.

An aspect of some embodiments of the invention relates to a holder (dop or base) in which a stone is clamped or clued for scanning, for providing minimal interference with the scan of the stone. In an exemplary embodiment the holder includes an upper and a lower cone for clamping the stone in place. Optionally, the holder further includes four wings surrounding the stone such that each two wings are parallel to each other and define a single obstruction in the scan process. Alternatively, only two wings or a single wing is provided. Preferably, the wings are thin in order to provide minimal obstruction to the scan process. Optionally, the wings have a thickness of about 0.5 mm. The inventors have found that the presence of two or four wings does not substantially impede the ability to locate the inclusions, especially if a large number of views of the gemstone are imaged.

In an exemplary embodiment, the stone is fixed on the same holder during external and internal scanning of the stone. Optionally, the holder is marked for correlation of the position of the stone between external and internal scanning. Optionally, at least one wing is marked by a notch on its side.

There is thus provided, in accordance with an exemplary embodiment of the invention, an apparatus for determining location of at least one inclusion in a gemstone having a first refractive index, comprising:

a container adapted for containing a material having a second refractive index, a holder operative to support a gemstone in the container and in the material when the container contains the material;

an illuminator positioned and adapted to illuminate said gemstone when disposed within said material in said container, with illumination at which said gemstone and said material have their respective first and second index of refraction;

a detector that detects illumination from the illuminated gemstone and said material and produces signals responsive thereto;

a controller that receives the signals and is operative to determine a location of an inclusion in the gemstone based on the signals; and a system, operative to reduce the presence within said material, at least when the gemstone is disposed therein, of any substance other than inclusions, having a third refractive index.

In an exemplary embodiment, a difference between said first and second refractive indices is in the range between 0 and less than 0.5 and between the first and third refractive index is our of said range. Alternatively, a difference between said first and second refractive indices is in the range between 0 and 0.1 and between the first and third refractive index is our of said range.

Optionally, the apparatus contains means for changing the orientation of one or more of said gemstone, said detector or said illuminator such that the detector detects said light in more than one such orientation.

Optionally, the detector is an image detector.

In an exemplary embodiment, the detector, the gemstone and the illuminator are disposed on one optical axis so that the detector detects light transmitted by the gemstone. In an exemplary embodiment, the gemstone is rotated around an axis which crosses said optical axis, such that signals representative of illumination incident on the gemstone from a plurality of directions, are produced by the detector and wherein the controller determines the position of inclusions based on such signals.

Optionally, the apparatus further comprises a heater for heating said material in solid form to become a liquid having said second refractive index, before said gemstone is disposed therein. Optionally, said heater surrounds the container to provide uniform heating of said material therein.

Optionally, the apparatus further includes means for controlling the uniformity of the temperature of the material at least along optical axis of the illuminator and detector.

In an exemplary embodiment, the material in said solid form is in the form of pellets before said heating.

Optionally, said system includes a device for the withdrawal of gas bubbles from said material before said gemstone is introduced therein. Optionally, said device is adapted for applying vacuum to the interior of said container.

Optionally, wherein said system is adapted for applying vacuum before and/or during heating of the material. Optionally, said system includes a source of an inert gas which is connected to the container so as to introduce said gas therein. Optionally, said source of inert gas is adapted for introducing inert gas to the container before the material is heated. In an exemplary embodiment, said source of inert gas is a source of helium.

In an exemplary embodiment, said container is sealable such that contaminants can not enter the container when it is sealed. Optionally, the container comprises a port for introducing the gemstone into the container while keeping the container sealed. Optionally, the port includes a passageway through which the gemstone passes on its path to the material said passageway being heated so as to heat the gemstone to a temperature approximately that of the material.

Optionally, the apparatus further comprises means for moving said gemstone into said material at a speed which is slow enough to prevent the entrance of gas bubbles into said material.

In an exemplary embodiment, said holder comprises a mechanism that clamps the gemstone between two points on the gemstone. Optionally, the two points are connected by a rigid structure.

In an exemplary embodiment, the apparatus further includes reference means for establishing a reference system for said detecting when disposed within said material in said container, in a plurality of orientations thereof, said reference means constituting a part of said holder. Optionally, said reference means comprises a scanner for scanning the external surface of said gemstone before its insertion in said material.

Optionally, said apparatus further includes means for obtaining an outline of an external structure of the gemstone, wherein said controller is adapted to correlate between said outline and said signals to determine the position of said inclusion relative to said external structure. Optionally, the means for obtaining is adapted to determine said outline of a gemstone having a coating thereon.

There is further provided, in accordance with an exemplary embodiment, a system for determining location of inclusions in a gemstone having a first refractive index, comprising:

the apparatus described above, adapted for performing the determination of said inclusions, under predetermined conditions; and a cleaning device for cleaning external surface of the gemstone, prior to its being introduced in said apparatus, from a medium other than possible inclusions, which either constitutes a substance having a third refractive index, whose difference from the first refractive index, when illuminated by said illumination, can cause artifacts, or is capable of producing such substance in interaction with said material or with the gemstone under said predetermined conditions.

Optionally, said cleaning device comprises sonication means for aiding said cleaning. In an exemplary embodiment, said cleaning device and said apparatus are adapted for mounting therein of a same holder for holding said gemstone. Optionally, said cleaning device is adapted for mounting therein of a plurality of holders of the kind mountable in said apparatus.

Optionally, said cleaning device comprises a container into which the gemstone is placed, the container containing a cleaning liquid capable of removing said medium from the external surface of the gemstone. Optionally, said cleaning device comprises a container into which the gemstone is placed, the container containing a cleaning liquid capable of removing said medium from the external surface of the gemstone and simultaneously cleaning a plurality of mounted gemstones.

There is further provided, in accordance with an exemplary embodiment, a device for cleaning external surface of a gemstone a cleaning container for cleaning external surface of the gemstone, from a medium adhering thereto;

a gemstone mount on to which gemstones held in a holder or dop can be mounted; and means for introducing the mounted gemstones into the cleaning container.

Optionally, the device further comprises sonication means for aiding said cleaning. Optionally, said mount is adapted for mounting therein of a plurality of gemstones. Optionally, said device comprises a container into which the mounted gemstone is placed, the container containing a cleaning liquid capable of removing said medium from the external surface of the gemstone.

There is further provided, in accordance with an exemplary embodiment, a holder for a gemstone comprising:

a mount for mounting the holder; and a holding mechanism that clamps the gemstone between two points on the gemstone.

Optionally, the two points are connected by a rigid structure. Optionally, the holder further includes reference means for establishing a rotational orientation of the holder. Optionally, the mount comprises a shaft.

There is further provided, in accordance with an exemplary embodiment of the invention, a method of determining the position of inclusions in a diamond gemstone, comprising:

(a) cleaning the diamond gemstone;

(b) placing the gemstone within a material having a refractive index within 0.1 of that of the gemstone;

(c) illuminating the gemstone and imaging the illuminated gemstone; and (d) determining the position of inclusions based on images of the inclusions in the images.

In an exemplary embodiment, the method further includes: repeating (b) and (c) for a plurality of orientations of the gemstone with respect to the illumination and an imager used to image the gemstone, wherein determining comprises:

determining the position of inclusions in three dimensional space based on images of the inclusions in the images.

Optionally, determining the position of inclusions comprises determining the external surface of the gemstone and determining the position of the inclusions relative to said external surface.

There is further provided in accordance with an exemplary embodiment of the invention a method of determining the position of inclusions in a gemstone, comprising:

scanning the external surface of a gemstone;

correlating the scanned surface with a precise outline of the external surface of the stone;

placing the gemstone within a material having a refractive index within 0.5 of that of the gemstone;

illuminating the gemstone and imaging the illuminated gemstone; and determining the position of inclusions relative to the external surface of the stone based on images of the inclusions in the images.

Optionally, scanning the external surface comprises scanning with an optical imaging device.

Optionally, the material is a liquid and placing comprises immersing the gemstone in the liquid. Alternatively, the material comprises a solid and wherein placing comprises encasing the gemstone in the solid.

Optionally, the illumination is in near-infra-red. Optionally, the illumination has a wavelength between 0.8 and 2 microns. Optionally the method further includes: coating the external surface of a gemstone with an opaque coating layer.

In an exemplary embodiment, the method further includes:

obtaining a geometrical representation of the external surface of a gemstone relative to a respective coordinate system, wherein imaging comprises obtaining a geometrical representation of the inclusions in the gemstone relative to the same coordinate system.

Optionally, said geometrical representation of the inclusions comprises color representation of the inclusions.

Optionally, the images comprise perceptible projections of the exterior of the gemstone and distinctive images of a non-deflected inclusion within a gemstone projection, such that a geometrical representation of the external surface of the gemstone can be obtained from said perceptible projections.

In an exemplary embodiment, obtaining the geometrical representation of the external surface includes irradiating the gemstone and determining a distance based on reflections from the surface.

In an exemplary embodiment, the method further includes: valuating the gemstone. Optionally, evaluating the gemstone includes determining one or more dividing planes for dividing the gemstone, based on the positions of the inclusions. Optionally, evaluating of the gemstone is responsive to the value of at least one potential polished gem yieldable by the gemstone.

Optionally, the value of the potential polished gems is responsive to the size and geometry of potential flawless polished gems. Optionally, the value of the potential polished gems is responsive to the size of the potential polished gems. Optionally, the value of the potential polished gems is responsive to the cost of producing these gems.

In an exemplary embodiment, the method further includes providing a plurality of sets of dividing planes each resulting in different sets of potential polished stones.

There is further provided, in accordance with an exemplary embodiment of the invention, a method of cleaning a rough gemstone of foreign substances, the method comprising:

removing foreign compounds from the surface of a rough gemstone;

washing the stone with a washing medium; and removing the washing medium from the stone.

Optionally, washing the stone comprises cleaning the stone and the washing medium is a cleaning medium. Optionally, removing foreign compounds comprises applying a surface active agent to the gemstone. Optionally, the surface active agent comprises an aqueous solution of surface active agent. Optionally, the aqueous solution of surface active agent comprises an anionic surfactant. Optionally, the aqueous solution of surface active agent contains chelating agent. Optionally, the aqueous solution of surface active agent is added with an additive having a moiety in its molecule that can compete with diamond in hydrophobicity. Optionally, the surface active agent comprises a cleaning solution used for cleaning optical devices. Optionally, applying a surface active agent comprises ultrasonic treatment with said surface active agent. Optionally, aqueous solution of surface active agent contains purified water.

In an exemplary embodiment, the washing medium comprises purified water. In an exemplary embodiment, removing the washing medium from the surface of stone comprises removing with a stream of air. Optionally, removing the washing medium from the surface of stone comprises removing with a stream of an inert gas. Optionally, removing the washing medium from the stone is followed by drying at elevated temperature.

In an exemplary embodiment, the method further comprises immersing the stone in a material having a refractive index within 0.5 of that of a gemstone.

There is further provided in accordance with an exemplary embodiment of the invention, a method of preparing a material comprising:

providing a gemstone having a refractive index;

filling a container with a material having a refractive index within 0.5 of the refractive index of the gemstone at a given wavelength and given temperature;

preventing contamination of the material;

controlling the temperature of the material in the container to the given temperature.

Optionally, controlling the temperature comprises increasing the temperature at least until the material melts. Optionally, the method includes removing bubbles from the material. Optionally, controlling the temperature comprises removing bubbles from the material in the container. Optionally, controlling the temperature comprises controlling the temperature such that a better mechanical match between the surface of the stone and the material is provided. Optionally, removing bubbles from the material in the container is carried out by heating the material under pressure of helium, followed by vacuuming the contents of the container. Optionally, removing bubbles from the material in the container is carried out by increasing the temperature and vacuum in the container.

In an exemplary embodiment, preventing contamination comprises vacuuming the container and filling the container with inert gas. Optionally, preventing contamination comprises maintaining inert gas atmosphere in the container.

In an exemplary embodiment, the method further comprises immersing the gemstones in the material. In an exemplary embodiment, the method further comprises imaging the gemstones in the material to determine the presence and position of inclusions in the gemstone. Optionally, the method further includes correlating the positions of the flaws with the external surface of the gemstone.

In an exemplary embodiment, the refractive index of the gemstone and the material are within 0.2. In an exemplary embodiment, the refractive index of the gemstone and the material are within 0.1.

Optionally, the material comprises a chalcogenide element in group 16. Optionally, the material comprises selenium. Optionally, the material comprises elemental selenium. Optionally, the material comprises thallium iodide. Optionally, the material comprises thallium bromide. Optionally, the material comprises a molten material.

Optionally, the material comprises one or more of antimony pentasulfide, antimony triiodide, antimony trisulfide, arsenic, arsenic disulfide, arsenic selenide, arsenic tribromide, arsenic triiodide, arsenic trisulfide, arsenous acid, chloro-chromic acid, chromic acid, cyanogen iodide, lead chromate, mercuric iodide, phosphorus, selenium, elemental selenium, selenium tetrachloride, selenium arsenic, bromine, iodine, silver bromide, silver chloride, silver iodide, sulfur, tellurium, tellurium chloride, thallium iodide-bromide, thallium monobromide, thallium monochloride, thallium monoiodide, stannic iodide, arsenic trichloride, piperine, boracic acid and lead chromate.

In an exemplary embodiment, the material and the gemstone are at a temperature of between 220 and 500 degrees Celsius.

In an exemplary embodiment, the material and the gemstone are at a temperature of between room temperature and 220 degrees Celsius.

In an exemplary embodiment, the gemstone is a diamond. Optionally, the gemstone is rough. Alternatively, the gemstone is polished.

There is further provided in accordance with an exemplary embodiment of the invention, an apparatus for evaluating of a gemstone, comprising:

an optical device adapted to scan the external surface of a gemstone;

a controller adapted to correlate the external scan of the optical device with an accurate outline of said stone;

a container adapted to include said stone and material having a refractive index within 0.5 of that of said gemstone;

a light source adapted to introduce light having a wavelength matching the temperature and refractive index of said material and light; and a detector adapted to detect light passing through said stone.

Optionally, said controller is adapted to indicate inclusions in the stone based on the light detected by said detector. Optionally, said controller is further adapted to indicate said inclusions relative to said outline of the stone.

There is further provided in accordance with an exemplary embodiment of the invention, a system for evaluating a gemstone, the system comprising of:

means for producing an accurate outline of an external structure of a gemstone;

means for scanning the external surface of said gemstone;

means for detecting inclusions in said gemstone; and means for correlating between said outline, said external scan and said inclusions.

BRIEF DESCRIPTION OF THE DRAWINGS

Non-limiting examples of embodiments of the present invention are described below with reference to figures attached hereto, which are listed following this paragraph. In the figures, identical structures, elements or parts that appear in more than one figure are generally labeled with a same symbol in all the figures in which they appear. Dimensions of components and features shown in the figures are chosen for convenience and clarity of presentation and are not necessarily shown to scale.

DETAILED DESCRIPTION OF EMBODIMENTS OF THE INVENTION

In the following discussion a possibly present inclusion (or flaw or defect) in singular applies as well to a plurality of inclusions.

Figure 6A:
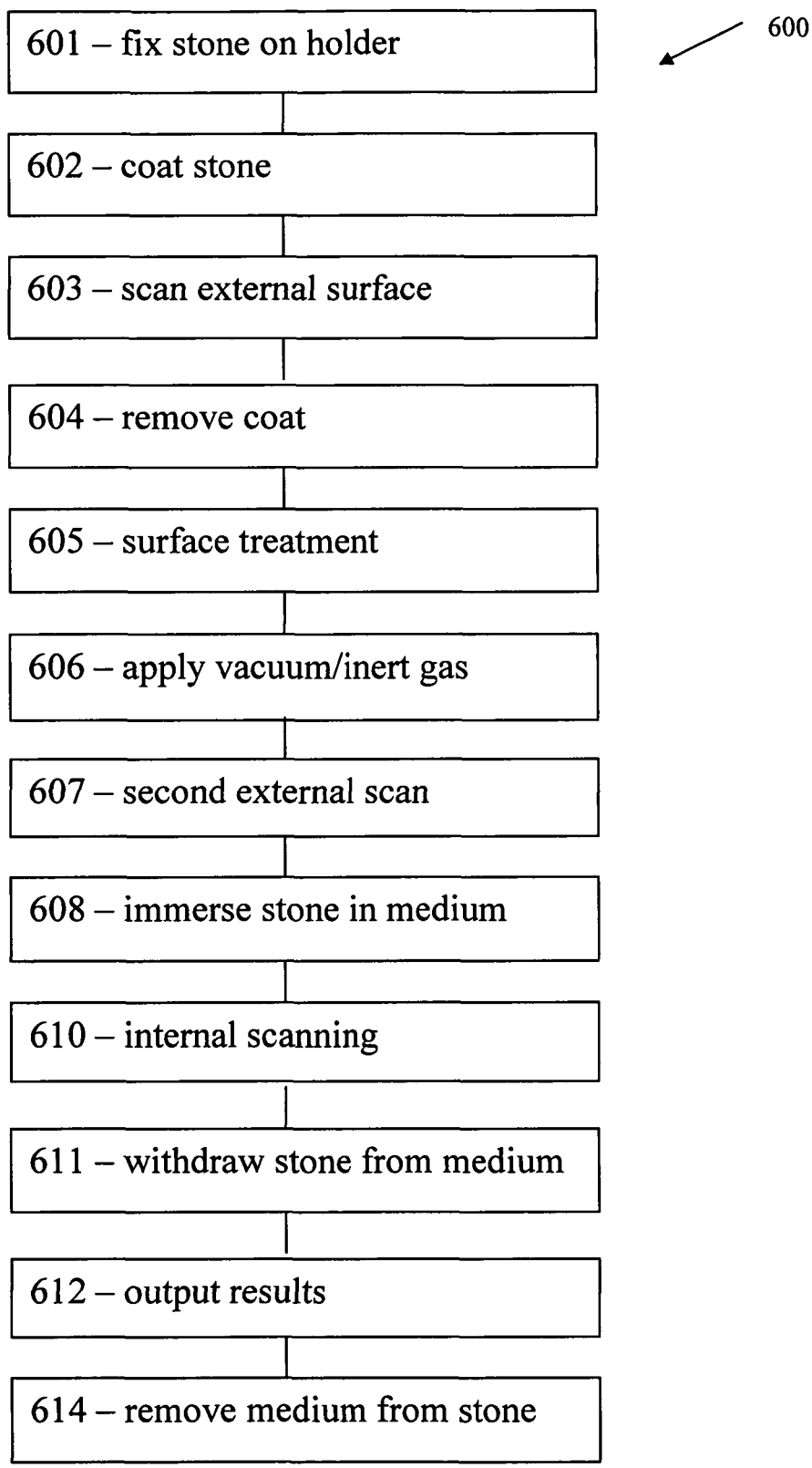
FIGS. 6A-6C are a flowcharts of a method of evaluating a gemstone, in accordance with an exemplary embodiment of the invention.

FIG. 6A is a flowchart of a method of evaluating a gemstone, in accordance with an exemplary embodiment of the invention.

First, the stone is clamped or glued to a holder or dop (601). In an exemplary embodiment, the stone remains clamped to the holder during the entire method of evaluation of the gemstone. Therefore the fixation means of the stone to the holder or dop should be resistant to all treatments of the stone and to the heated immersion medium. In addition, for efficiency of the evaluation method, the fixation should preferably be performed in a short time and be easily removable after evaluation of the stone. Preferably, the stone is fixed on the holder by clamping or screwing. Alternatively, the stone is fixed on the holder by glue. Care should be taken when using glue since glue is liable to be released in the heated immersion medium which is used in the process described below, thereby contaminating the medium. Alternatively, the stone is soldered to the holder, however, soldering may damage the stone.

Figure 8:
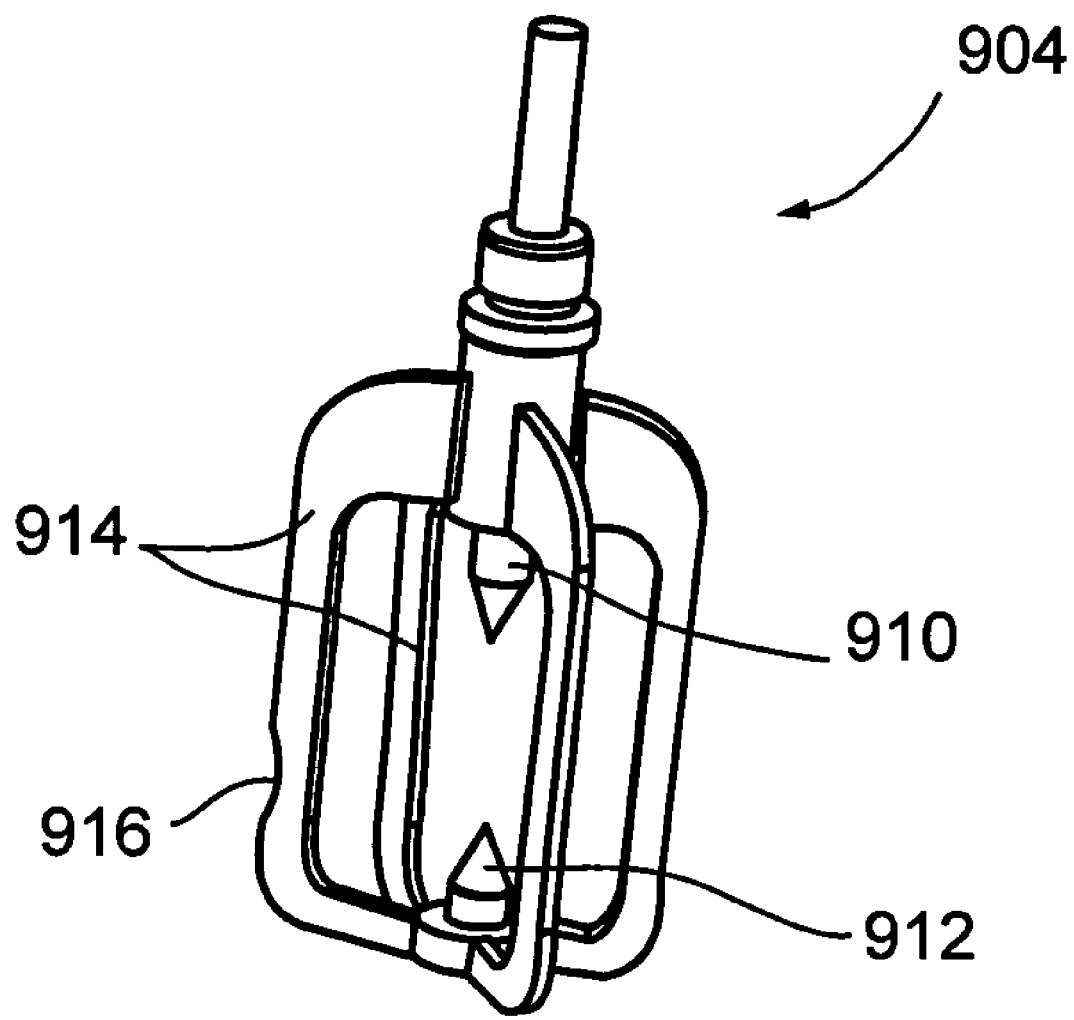
FIG. 8 is a schematic illustration of a holder for fixing a stone in accordance with an exemplary embodiment of the invention.

Optionally, a holder as shown in FIG. 8 is used. The stone may optionally be cleaned, for example, by acid-boiling, as known in the art, before the stone is mounted on the holder.

Optionally, the stone is coated (602), before or after clamping the stone to the holder (601) by a uniform coat layer before scanning to provide a high enough reflectivity from a light source used during scanning of the external surface of the stone, as described below. Optionally, the coat layer has a thickness of a 1, 2, 3 or any intermediate or larger number of microns. Optionally, the coat layer is an opaque coating layer.

The external surface of the stone is scanned at 603 and a reconstruction of the outer surface of the stone is obtained. The external scanning or determination of external surface process according to an exemplary embodiment of the invention will be described in greater detail with reference to FIG. 1 below.

Optionally, if the stone was coated before scanning, the coat layer is removed (604) after scanning. The coat layer may be removed by washing the stone with organic solvents like acetone or an alcohol, such as ethanol or isopropanol or with aqueous cleaning solutions. Optionally, ultrasonic treatment (sonication) is applied to the stone when in a cleaning medium to assist in removing the coat layer of the stone. Optionally, removing the coating from the stone (604) is performed along with cleaning of the stone and holder at 605.

Optionally, the surface of the stone is treated or cleaned (605) in order to remove all foreign substances that may be present at the surface of the stone. Optionally, the holder on which the stone is clamped is also cleaned together with the stone. The surface of the stone is preferably cleaned since the stone may be contaminated due to adhesion of vapors of organic compounds and inorganic compounds, such as solid particles etc., which are usually present in the environment. This may cause the presence of substances at the surface of the stone that may be non-transparent at the light wavelength used in the internal scanning process (610), and observed as black areas that may prevent observation of or mimic defects at the surface and inside the stone. These materials may also react with an immersion medium used in the internal scanning process.

Surface treatment is especially suggested with diamonds since diamonds are known for their hydrophobic properties and have an exceptionally high ability to attract other species of hydrophobic nature. The compounds adhered to the diamond surface usually have a dual hydrophobic-hydrophilic nature. It is believed that when the compounds stick to a diamond, their hydrophilic part is exposed outward the diamond surface and adhere hydrophilic molecules of oxygen, carbon dioxide and other gases which may be present in the environment. The compounds adhered to the surface of the diamond form bubbles at the surface of the diamond when the diamond is immersed in the immersion medium (608), and are observed as black bodies, that present as spurious flaws in the gemstone and/or obscure true flaws. In addition, the presence of hydrophilic moieties on the diamond surface may cause the immersion medium to adhere to the diamond surface after withdrawal of the diamond from the immersion medium.

Figure 6B:
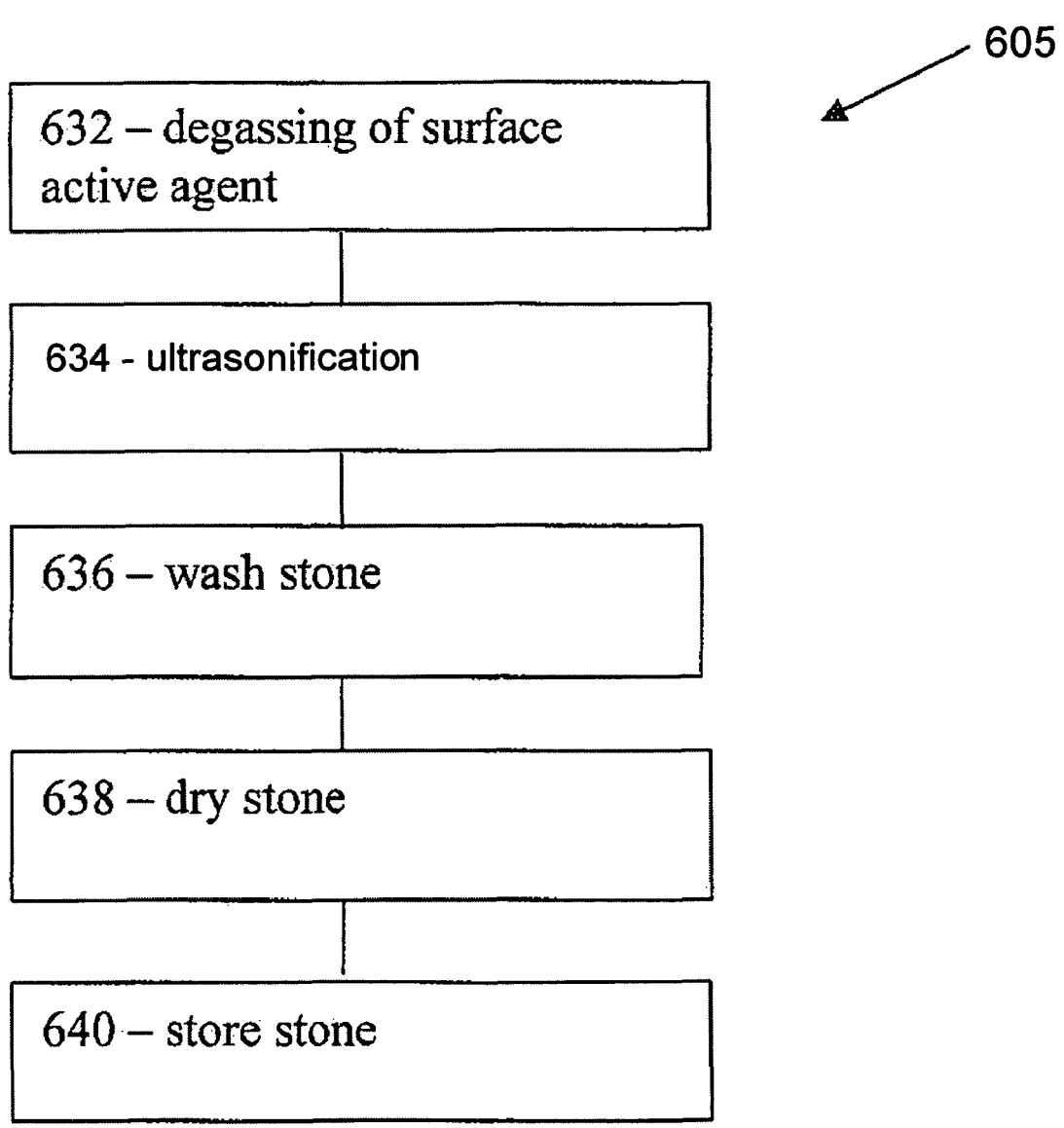

FIG. 6B is a flowchart of a method 605 of surface treatment of a gemstone in accordance with an exemplary embodiment of the invention. In an exemplary embodiment of the invention, the surface treatment is aided by sonication in an aqueous solution of a surface active agent. A surface active agent according to an exemplary embodiment may be one or more of anionic, cationic, nonionic or ampholytic type or their combination. Optionally, the surface active agent is an anionic surfactant (like sodium dodecyl sulfate (SDS)).

Optionally, the surface active agent is sodium salt of dodecylbenzenesulfonic acid. Optionally, the aqueous solution of surface active agent contains a chelating agent like disodium salt of ethylenediaminetetraacetic acid ($Na_2.EDTA$). Optionally, the aqueous solution of surface active agent can be added with other additives that contain hydrophobic moieties like 1-phenoxy-2-propanol or 1-phenoxy-2 ethanol. Optionally, pH of the aqueous solution of surface active agent is adjusted within 6-10.

Optionally, the surface treatment is improved by using a surface active agent in combination with dispersants and emulsifying agents. Optionally, commercially available cleaning solutions, such as solutions used for cleaning optical devices, for example a cleaning composition Hellmanex™ by Hellma GmbH & Co., are used.

It should be noted that according to an exemplary embodiment of the invention, some, all or none of the acts depicted in method 605 may be taken. Optionally, method 605 is performed by the apparatus depicted in FIG. 7.

Optionally, at 632 the solution of surface active agent is degassed, optionally, while applying ultrasound. The gemstone is then placed in an aqueous solution of surface active agent (634) and subjected to sonication. The cleaned stone may then be washed with purified water (636). Optionally, moisture is removed from the surface of the stone by treating the stone (638) with a stream of clean air or inert gas. Optionally, the stone is heated to accelerate the drying process. Optionally, the cleaned stone is then stored (640) at atmosphere of an inert gas such as helium, or under vacuum. Optionally, helium gas is used to dry the surface of the stone and the stone is stored, if necessary in a helium atmosphere or under vacuum. Alternatively, some other inert gas is used.

An exemplary procedure for treating the surface of a diamond, clamped to a holder, may be as follows:

1. Sonication of the diamond in the SDS solution for 15 min at 70° C. incl. (634);
2. Three times repeatedly washing the diamond in purified water, with appliance of ultrasound, for 5 min each time at 70° C. (636);
3. Draining the purified water from the container in which the stone is positioned;
4. Drying the diamond by heat (638); and
5. Storing the diamond clamped on its holder in a closed container.

Figure 7:
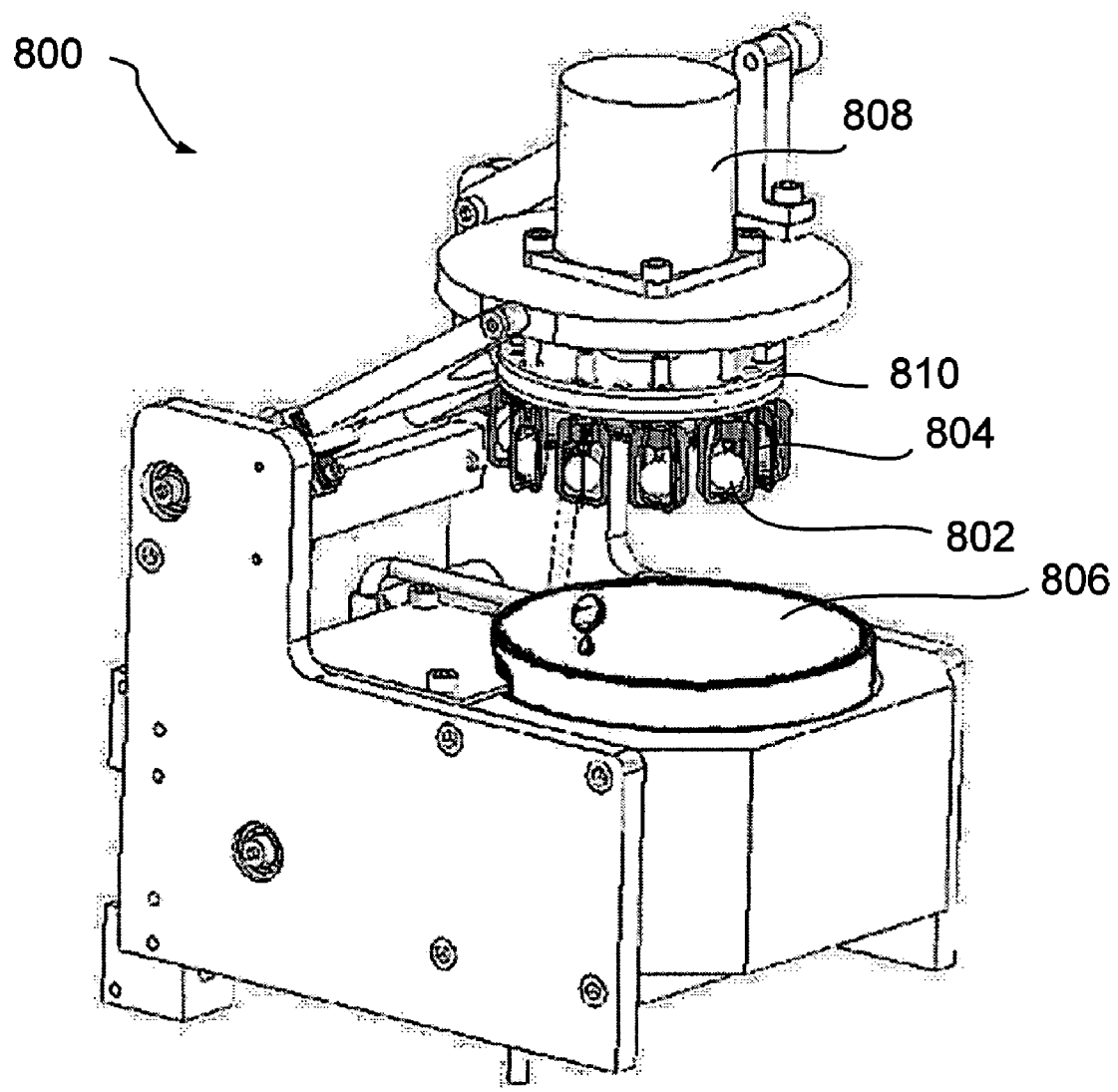
FIG. 7 is a schematic illustration of a system for cleaning stones according to the method described in FIG. 6B in accordance with an exemplary embodiment of the invention.

FIG. 7 is a schematic illustration of a system 800 for cleaning stones according to the method 605 as described in FIG. 6B in accordance with an exemplary embodiment of the invention. According to this embodiment, a plurality of stones is cleaned in a single process. Stones 802 are shown as clamped to holders 804. The stones in the holders are mounted on a rotatable carousel 810 which is immersed into receptacle 806 for the cleaning process. Receptacle 806 is first filled with a solution of surface active agent Optionally, the cleaning medium is heated to 70° C. Optionally, an ultrasonic resonator (not shown) is provided around receptacle 806 which produces ultrasound and applies sonication in the receptacle to assist in the washing process.

The cleaning medium is then removed from the receptacle and replaced with purified water. Optionally, washing of the stones with purified water is repeated several times, for example three times. The cleaning process is terminated by removing the water from the receptacle and drying the surface of the stones. Optionally, drying is performed by one or more heaters (not shown) positioned around receptacle 806. In an exemplary embodiment of the invention, motor 808 rotates the carousel continuously or interrupted to assist in the cleaning process.

Referring back to FIG. 6A, optionally, a second external reference scan (606) of the stone is taken for correlation of the stone position with the external scan performed ad 603. the reference scan may be taken at any time before immersing the stone in the immersion medium (608).

The material used for the immersion medium may be sensitive to foreign substances present in air. For example, when selenium is exposed to air, the selenium may produce selenium dioxide that may adversely affect the optical properties of selenium. In addition, contact of hot selenium with moisture present in air may result in formation of selenium dioxide and hydrogen selenide. In addition, when selenium is exposed to oxygen, the substances in the air tend to adhere to the surface of the stone, thereby creating bubbles and be observed as black areas that may prevent observation of or mimic defects at the surface and inside the stone.

Air is liable to penetrate into the container with immersion medium at the time of immersing the stone in the medium. Therefore, vacuum and/or inert gas is applied (606) in order to remove foreign substances from the surface of the stone and holder and their surroundings and prevent contamination of the medium by foreign substances. Application of vacuum or inert gas (666) may also be used in order to dry the stones from the moisture remaining on the stone surface from cleaning method 605. Optionally, and preferable when the immersion medium comprises selenium, helium is used as the inert gas. Optionally, helium is applied at between at 0.1-0.5 atmosphere gauge (over) pressure. Optionally, vacuum and helium are repeatedly applied until a desired atmosphere is achieved in the container, for example about 0.1-0.2 at gauge pressure, is reached.

Since the index of refraction change according to temperature, the stone is preferably heated before immersed in the medium such that the temperature of the stone and medium match when immersed. Optionally, the stone is heated by passing through a heated passageway to the container with the immersion medium. Alternatively, the stone is heated by the medium. Optionally, the temperature is 220° C. Alternatively, the temperature is between 230° C. and 240° C., optionally 235° C.

Preferably, immersing or disposing the stone in the medium (608) is performed at a controlled rate. Optionally, the stone is immersed at a slow rate in order to avoid bubbles being adhered to the surface of the stone and/or heat the stone during immersion. The slow rate may be a few mm per second or less than 1 mm/sec. Optionally, the stone passes through an atmosphere of helium, covering the immersion medium to avoid penetration of air during immersion. Optionally, the container with the immersion medium is lifted to the stone instead of lowering the stone in the medium.

The stone is disposed in an immersion medium and internally scanned for detecting the presence and/or location of inclusions in the stone (610), as will be further detailed with respect to FIGS. 2A-C below. After internal scan of the stone, the stone is withdrawn from the immersion medium (611) and the results of the internal scan are outputted (612). Optionally, the stone is withdrawn from the medium (611) after the output of the results (612). The computation of the results of the signals detected by the internal scan will be further detailed with respect to FIGS. 3-5 below.

In an exemplary embodiment, 606-612 are performed in the same apparatus.

At 614 the stone is cleaned to remove materials that may be present on the stone surface. The cleaner the stone is prior to immersion, the less immersion medium (e.g., Se) is adhered to the stone surface. A slow immersion of a holder with stone into immersion medium at a controlled rate assists in avoiding bubbles adhering to the stone surface. In addition, a slow withdrawal of a holder with stone from immersion medium at a controlled rate assists in minimizing the amount of adhered Se. Further, a fast cooling of the withdrawn diamond allows formation of Se in amorphous form at the stone surface and facilitates removal of Se by chemical means.

Optionally, when the immersion medium is Se, the extracted stones may be cleaned to remove Se by one or more of the following chemical methods:
- treatment with a hot nitric acid;
- heating in a hot sulfuric acid with or without addition of oxidation agents such as sodium dichromate, potassium nitrate, hydrogen peroxide etc;
- treatment with aqueous solution of potassium cyanide
- heating in an aqueous solution of sodium sulfite; or
- other methods known from the chemistry of Se.

From a safety and environmental point of view, the treatment with sodium sulfite is a preferred method for removal of Se.

The cleaned diamonds are further washed with purified water.

In an exemplary embodiment, the cleaning process 614 is similar to the cleaning process 605 and may both be performed by the device depicted in FIG. 7. Optionally, cleaning process 614 is performed at an elevated temperature, for example at around 100° C. or 97° C.

Figure 6C:
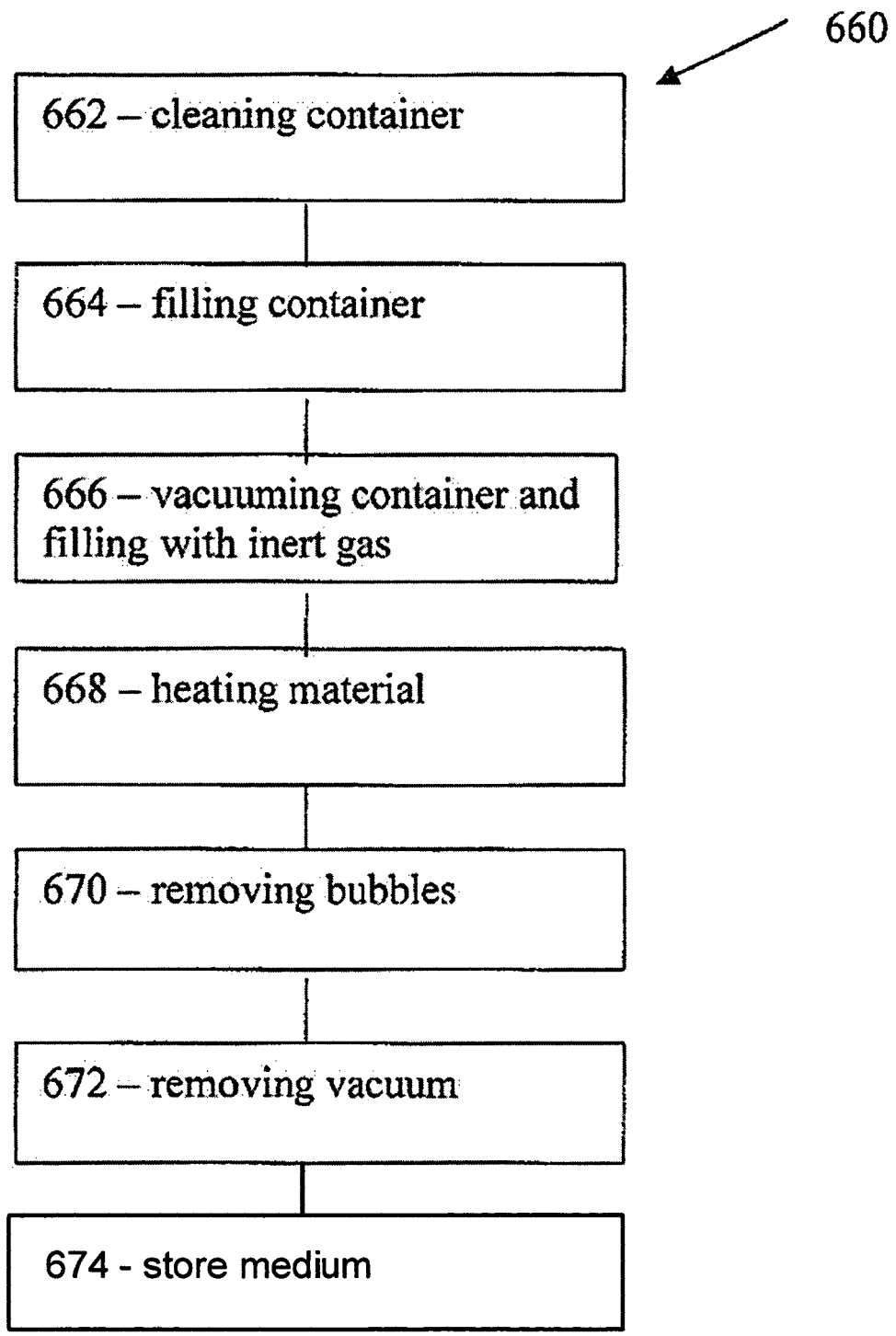

FIG. 6C is a flowchart of a method 660 of preparation of an immersion medium for internal scanning of a stone in accordance with an exemplary embodiment of the invention. The immersion medium may be prepared at any time before immersing the stone in the immersion medium. In an exemplary embodiment, the prepared immersion medium may be used for a number of internal scans, such as 100, 1000 or more. Optionally, new medium is prepared only when the medium is contaminated or used up.

In an exemplary embodiment, the immersion medium preferably has two requirements: (1) a refractive index substantially matching to that of the stone and (2) providing a satisfactory image quality for further image processing. This second requirement generally means that the mechanical match between the stone and the material should be good, and that the immersion medium is not contaminated with gas bubbles and other foreign matter. Optionally, the immersion medium complies with other requirements, such as being in a liquid or gel state, easy preparation, simple handling, acceptable toxicity, and chemical stability in environment with no change in refraction index over time.

Following are exemplary immersion media that can be used for diamonds in accordance with an exemplary embodiment of the invention. Preferably, pure elementary substances, such as pure selenium are used since compounds do not always behave uniformly when heated or over time.

1. A selenium-based immersion medium containing Se only, or in combination with other components which can be selected, for example, from those used in the preparation of Se-based chalcogenide glasses, and may include sulfur, germanium, antimony, arsenic, tellurium, silicon, silver, phosphorus, lanthanum, indium, thallium, iodine, bismuth, lead, copper, gallium, tin etc. or their compounds such as arsenic disulfide, arsenic triselenide, etc.

Optionally the immersion medium comprises elemental selenium or is composed substantially only of elemental selenium.

Optionally, the Se-based medium is heated to a temperature of between 230 and 240 degrees Celsius and infrared light of wavelength approximately of between 1.1 and 1.2 micrometers is used for internal scanning as the refraction index of selenium is substantially close to that of diamonds under these conditions. Optionally, a temperature of 235° C. and wavelength of 1.14 is used. Alternatively, the Se-based medium is heated to a temperature of 235 degrees and the same wavelength of near infrared light is used.

Optionally, the diamond may be immersed in molten material which subsequently solidifies, encasing the stone in a solid phase. Optionally, the molten material is molten selenium. Optionally, the selenium is mixed with a material that forms a gel. This may enable working at lower temperatures and providing better matches. For example, at a temperature of around 230 degrees Celsius and a wavelength near 1.2 micrometers there is low loss of selenium and a good match between the refraction index of diamond and selenium. Preferably, the solid selenium is in an amorphous form.

It is understood that increasing the temperature of the immersion medium and the diamond has some important effects. On the one hand, the viscosity of the selenium decreases, making for a better mechanical match between the rough surface of the stone and the medium, while vapor pressure of selenium increases. On the other hand, the refraction index of the medium and the stone changes with temperature. Thus, the temperature and wavelength should be chosen to reflect a balance between these factors. Under various conditions, in various preferred embodiments of the invention, the wavelength may vary from 0.8 micrometer to 2 micrometers, and the temperature from room temperature to 500 degrees Celsius. Optionally, the temperature may vary from 100 to 400 degrees Celsius and the wavelength from 1 micrometer to 1.2 micrometers. Optionally, the temperature is between room temperature and 250 degrees Celsius or between 220 and 250 degrees Celsius.

It should be noted that in accordance with an exemplary embodiment of the invention, substantially pure elemental Selenium is preferably used as the immersion medium.

2. A Sulfur-based immersion medium containing such components as selenium, arsenic, tellurium, arsenic disulfide, mercuric iodide, arsenic trisulfide, arsenous acid, bromine, iodine, etc. and combinations thereof.

3. Thallium iodide-bromide. Optionally, the immersion medium is a mixture consisting of 46 mol % thallium bromide and 54 mol % thallium iodide is used. This medium has a melting point of 410° C. and a refractive index of 2.44 at 1.06 μm ad 2.40 at 10.6 μm.

Note that these values are extracted from U.S. Pat. No. 4,521,073, the disclosure of which is incorporated herein by reference. Products based on thallium iodide-bromide are sold under a name KRS-5. See, for example http://www.crystran.co.uk/products.asp?productid=86)

4. Immersion liquid composed from the following compounds and combinations thereof, having a high refractive index. Since the below listed compounds and their combinations are solids at normal conditions, they should be used in a molten state or as a solution in appropriate solvent or mixture or solvents.

A. Antimony pentasulfide
B. Antimony triiodide
C. Antimony trisulfide
D. Arsenic
E. Arsenic disulfide
F. Arsenic selenide
G. Arsenic tribromide
H. Arsenic triiodide
I. Chloro-chromic acid
J. Chromic acid
K. Cyanogen iodide
L. Lead chromate
M. Mercuric iodide
N. Phosphorus
O. Selenium
P. Selenium tetrachloride
Q. Silver bromide
R. Silver chloride
S. Silver iodide
T. Sulfur
U. Tellurium
V. Tellurium chloride
W. Thallium monobromide
X. Thallium monochloride
Y. Thallium monoiodide
Z. Stannic iodide
AA. Arsenic trichloride
BB. Piperine
CC. Boracic acid
DD. Lead chromate It should be noted that the above listed compounds are referred to in Meyrowitz, R., "Immersion Media of High Index of Refraction" mentioned in the background. Meyrowitz also lists the refractive index of these compounds. Since these compounds, if taken individually, do not perfectly match the refractive index of diamonds, in some embodiments of the invention, these compounds are used in combination with other compounds and/or solvents having a high refractive index.

In an exemplary embodiment of the invention, the following compounds or combinations thereof are used as the solvents to facilitate the dissolving of the above listed high refractive index compounds, as the following compounds have a high refractive index (above 1.65):

A. Mercuric iodide
B. Arsenic tribromide
C. alpha-Bromonaphthalene
D. Cacodyl selenide
E. Carbon disulfide
F. Diethylselenium
G. Dimethylmercury
H. alpha-Iodonaphthalene
I. Methylene iodide
J. Phenyl di-iodoarsine
K. Phosphorus
L. Selenium monobromide The immersion medium is optionally liquid or gel-like. Optionally the medium comprises at least one chalcogenide element in group 16 of the periodic table, such as sulphur, selenium or tellurium.

Optionally, the material is mixed with a material that forms a gel. This may enable working at lower temperatures.

The requirements of the immersion medium, such as temperature, refraction index and clarity, should preferably be constant and not vary over time.

One or more of the following actions may be taken in order to ensure the stability of the immersion medium:

1. raw material of appropriate purity
2. initial preparation of optically clean immersion medium;
3. keeping operating parameters, such as temperatures and/or pressure, constant;
4. avoiding thermal gradients throughout the measurement container;
5. preventing contamination of the immersion medium which may be a result of oxidation of the immersion medium by air, penetration of moisture and volatile or gaseous compounds to measurement container, chemical interaction of immersion medium with construction materials or introduction of impurities with holder or stone.

It should be noted that according to an exemplary embodiment of the invention, some, all or none of the steps depicted in method 660 may be taken.

In an exemplary embodiment of the invention a rectangular (or other shaped) measurement container, such as a cuvette, having two opposite optical windows is used. Preferably, the two optical windows are parallel to each other, flat and perpendicular to the optical axis used during internal scanning, as explained with reference to FIG. 2B below, such that there is no optical deviation while the light moves from the high index medium to the air. Alternatively, the container has an arbitrary shape (e.g. cylinder), and the optic comprises a compensation lens for elimination of the refraction of the light, resulting from the cylindrical shape, while moving from the high index medium to the air. Optionally, when the immersion medium is Se based, the cuvette is made of Pyrex or fused silica (quartz) since these materials are the most inert to Se.

In an exemplary embodiment the external surface of the cuvette is coated by non-reflecting coating. Optionally, the internal surface is also coated by a coating for avoiding reflection of the light by the cuvette. Other lenses and windows in the system may also be coated by non reflected coating. In some embodiments of the invention, no coating is necessary and a standard cuvette, such as Starna® Type 96 may be used.

Optionally, prior to filling the container, the container is cleaned (662) with conventional cleaning treatments for optical surfaces.

The container is then filled with the immersion medium or the compounds composing the immersion medium at 664. Preferably pellets of the compounds are used, since powder has a low bulk density and contains a large amount of entrapped air, and is less convenient for application of vacuum. In order to prevent contamination of the immersion medium, air is evacuated from the container and the container is filled with inert gas, such as helium, at 666. Optionally, only inert gas, without vacuum, is applied at 666. Optionally, 666 is repeated, for example, two or three times.

The temperature of the immersion medium is then increased (668). Optionally, the temperature is increased in order to make a better mechanical match between the stone and the medium, as, for example, increasing temperature causes selenium to melt and the viscosity of selenium to decrease. Optionally, the container is surrounded by a plurality of heating elements in order to provide uniform heating of said material therein.

Optionally, bubbles are removed from the medium at 670. Optionally, the bubbles are removed by methods similar to those used for refining glass, namely a gas blowing method (saturation of melt with a light gas like helium), a reduced pressure method, a sonic/ultrasonic method, reduction of viscosity by increasing a temperature, reduction of viscosity by using additives, etc. and combinations thereof.

Optionally, removing of bubbles is performed by decreasing pressure in the container by applying vacuum. Alternatively, bubbles are removed by further increasing the temperature and vacuum in the container.

At 672 vacuum is removed by addition of an inert gas (preferably helium) and setting a slight excess pressure of helium, such as 0.1-0.2 bar gauge pressure. It is noted that according to an exemplary embodiment of the invention, bubbles may be removed by both 670 and 672 or only one of 670 and 672. Optionally, 670 and 672 are repeated until the desired atmosphere in the container is reached. Optionally, 668, 670 and 672 are simultaneously performed.

The immersion medium is then stored (674), optionally in a sealed container to avoid contamination of the medium. Optionally, the sealed container has an opening for continuously applying a slight pressure of inert gas to maintain the atmosphere in and surrounding the medium. For example atmosphere of helium at about 0.1-0.2 atmosphere gauge pressure is maintained over the immersion medium.

In an exemplary embodiment of the invention, the medium is prepared by the following method:
  filling the measurement cuvette with Se pellets (664);
  3-fold vacuuming (to ~5 torr) the cuvette followed by filling with an inert gas (such as helium) at 0.1-0.5 atmosphere gauge pressure (666);
  gradually increasing temperature of Se in the inert atmosphere (e/g., helium) at a slight excess pressure of inert gas to 240° C. (668);
  optionally maintaining Se at 240° C. for additional 20 min decreasing pressure in the cuvette to atmospheric pressure;
  applying vacuum of ~1 torr until disappearance of bubbles in the immersion medium (668); and
  adding an inert gas such as helium at a slight excess pressure of the gas.

Alternatively, the medium is prepared by the following method:
  filling the measurement cuvette with Se pellets (664);
  3-fold vacuuming (to ~5 torr) the cuvette at followed by filling with inert gas at 0.1-0.5 at (668);
  gradually increasing temperature of Se to 240° C. at vacuum of ~1 torr;
  continuing heating at the temperature and vacuum until disappearance of bubbles in the immersion medium (670); and
  removing the vacuum by adding an inert gas such as helium and setting a slight excess pressure of helium (672).

Alternatively, the medium is prepared by the following method:
  1. Three-fold treatment with vacuum-helium to remove air from the container and medium;
  2. heating under slight excess pressure of helium to ~220-240° C.;
  3. releasing helium pressure;
  4. applying vacuum until complete disappearance of gas bubbles from immersion medium and windows of container;
  5. removing vacuum by adding helium and maintaining an atmosphere of helium during further operation of container; and
  6. adjusting operating temperature, if required.

Or the following method:
  1. Three-fold treatment with vacuum-helium to remove air from the container and medium;
  2. heating under 1-2 torr vacuum to ~220-240° C. until complete disappearance of bubbles from immersion medium and windows of container;
  3. removing vacuum by adding helium and maintaining atmosphere of helium; and
  4. adjusting operating temperature, if required.

Optionally, an inert gas, such as helium, is streamed to the surroundings of the stone during the immersion of the stone in the medium, which assist in avoiding bubbles and contamination of the medium by air or other foreign substances.

Figure 1:
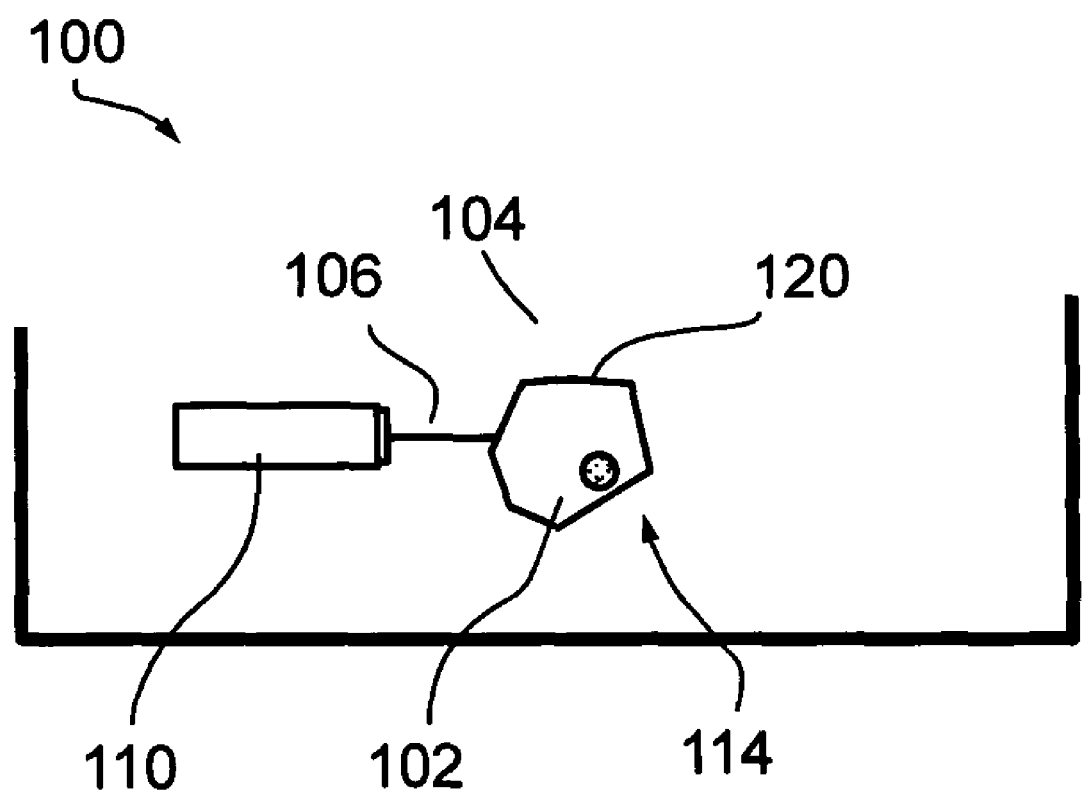
FIG. 1 is a schematic illustration of an imaging apparatus to determine the external structure of a gemstone, in accordance with an exemplary embodiment of the invention.

An apparatus 100 for the determination of the external structure of a gemstone, according to an exemplary embodiment of the invention, is schematically illustrated in FIG. 1.

The apparatus 100 may be replaced by any method known in the art for determining the external structure of a gemstone.

Face 120 of a gemstone 102 (optionally with a substantially flat surface (floor) 114) is fixed on a rotatable base 104 of a known position and orientation by any method known in the art, such as mechanical grip, vacuum or gluing. Optionally, base 904 shown in FIG. 8 is used.

An optical probe 110 with known position, measures the distance 106 to the stone of the light extracted from a light source in probe 110. Optionally, a separate light source is provided. The stone is scanned to provide a map of the external surface of the stone in the coordinates of the measuring system. In order to capture the stone from various points of view, the stone may be rotated around an axis during scanning. Alternatively, probe 110 is rotated during scanning.

In an exemplary embodiment of the invention, optical probe 110 comprises a plurality of spot probes that each measure one point on the object at a time. Alternatively or additionally, a number of optical probes 110 are used to measure the distance from the stone from different aspects thereof. Alternatively or additionally, optical probe 110 has a wide angle view, for example between 100 and 180°. Probe 110 measures distance 106 for a plurality of light points when the stone is rotated and results a point cloud of distances.

Optionally, the external scanning process is repeated two or more times to increase accuracy. Optionally, stone 102 may be fixed to base 104 in a different position for a supplemental scanning process, such that face 120 that was fixed on base 104 will be scanned in the supplemental scanning process. The point clouds received from the different scanning processes are then merged to one point cloud. The merge to one point cloud may be performed by any method known in the art and is generally very accurate. The merged point cloud is then interpolated to provide a surface description of the stone.

Optionally, when the same base (holder) is used for internal scanning the base rotation angle is used as a reference for both the external scanning and the determination of the surface of the stone Optionally, the resolution of the scanning is 30 micron step while the measuring spot is 8 micron and accuracy of 1 micron of depth.

Figure 2A:
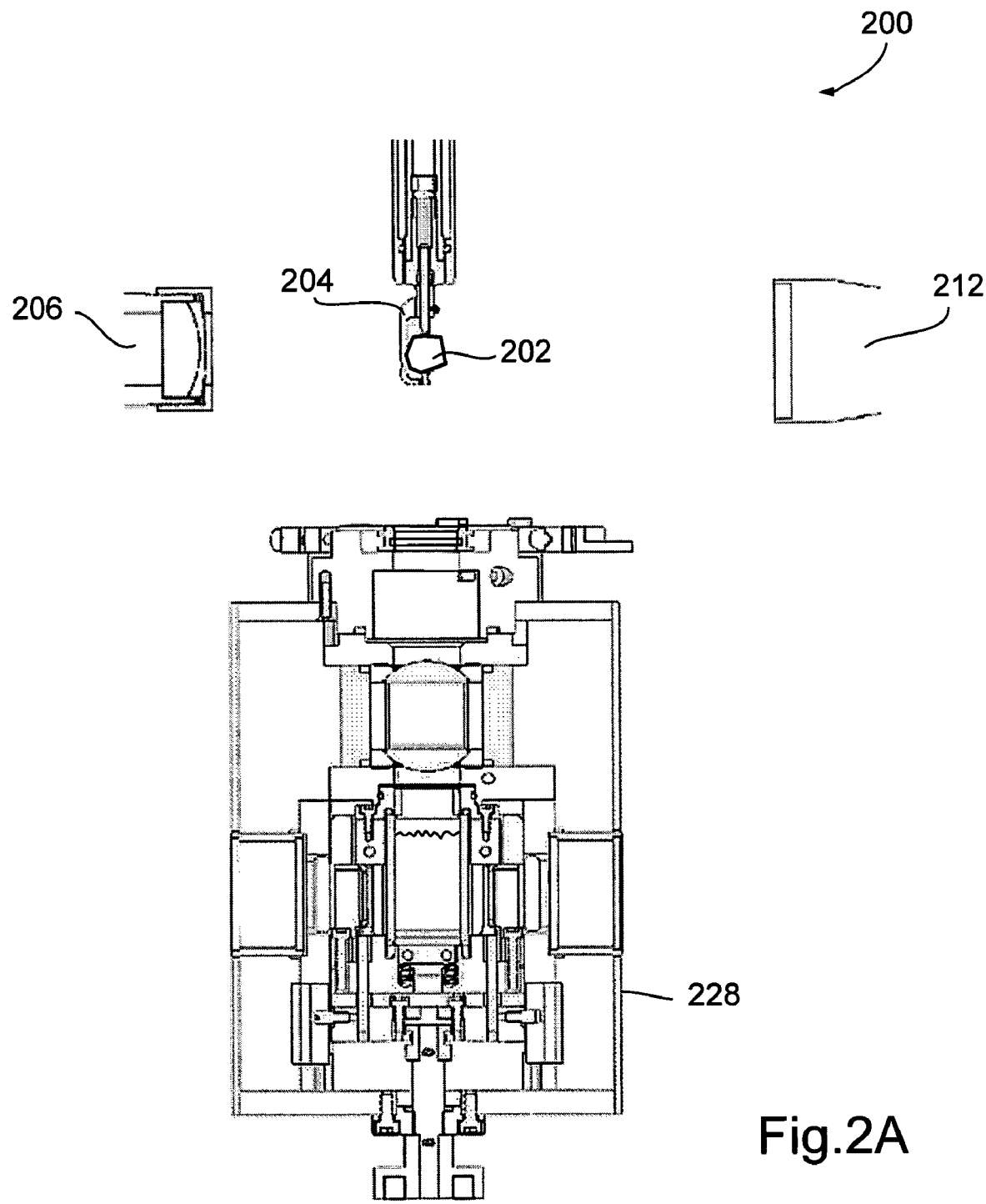
FIGS. 2A-2C are schematic illustrations of the use of an apparatus to determine the position of an inclusion in a gemstone, in accordance with an exemplary embodiment of the invention.
Figure 2B:
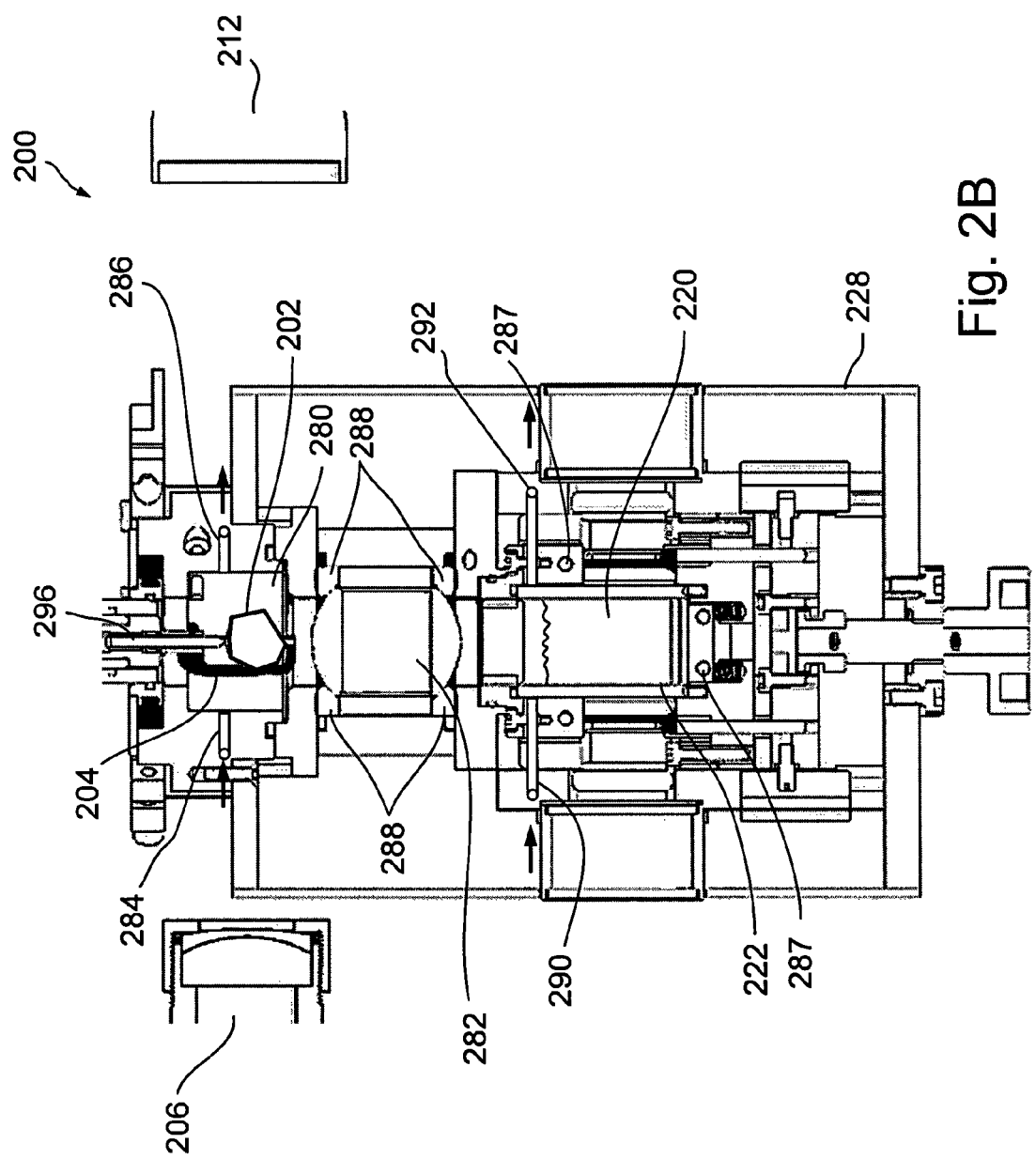
Figure 2C:
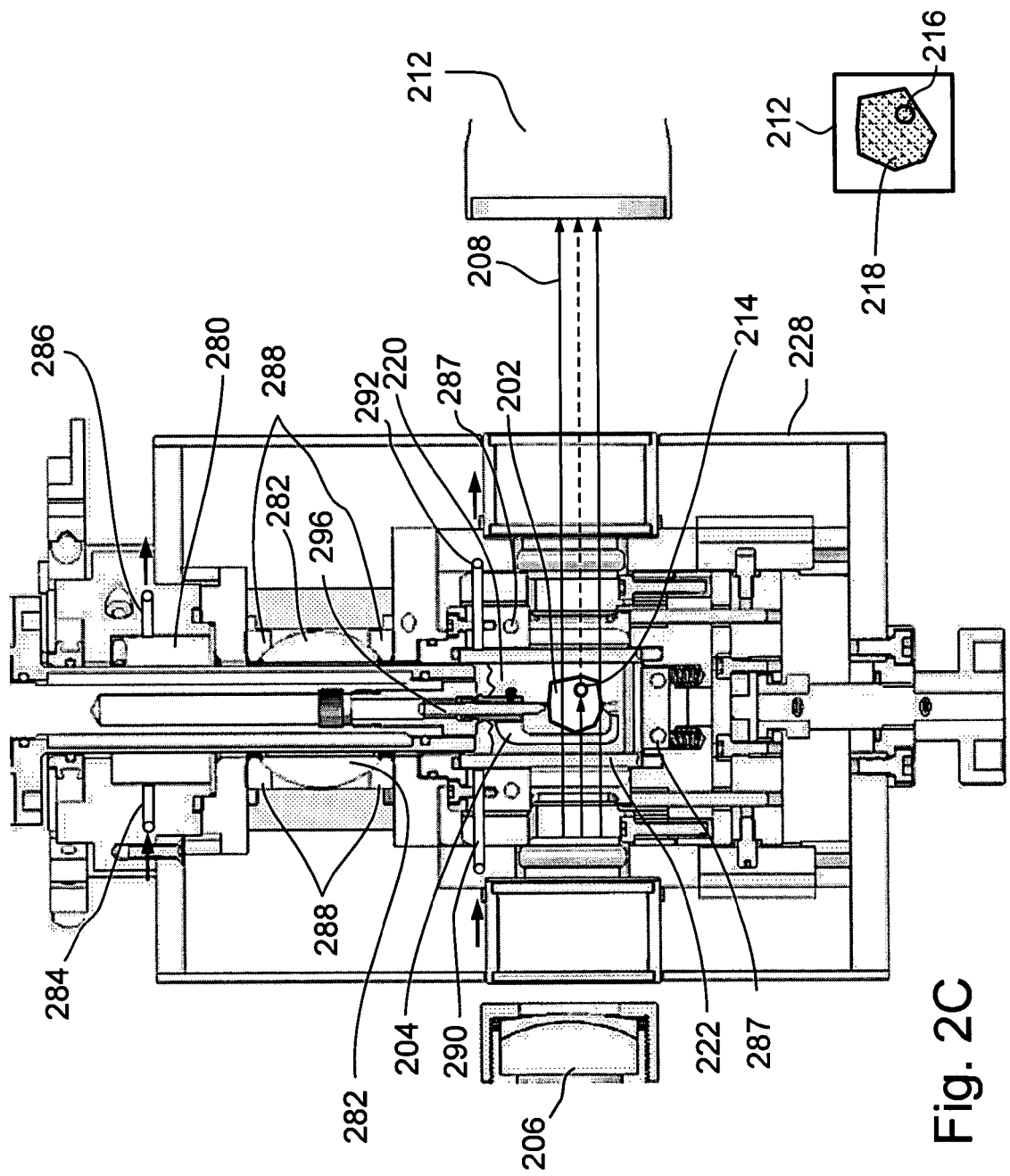

FIGS. 2A-2C schematically illustrate an apparatus 200 for the determination of the positions of inclusions within a stone 202 fixed on a holder 204. Apparatus 200 comprises a cabin 228 which includes a compartment 280 and a container 222. Apparatus 200 further includes an optical imaging device or detector 212 for detecting the light originated from a light source 206.

Stone 202 is shown in FIG. 2A as positioned in system 200 in a position for determining reference of the external structure of gemstone 202. The external reference scanning by system 200 is optionally less accurate than the external scanning of apparatus 100 in FIG. 1. In an exemplary embodiment, the external reference scanning with system 200 is used only to correlate the position of the stone on holder 204 with the accurate external scanning received from device 100, which is performed as well. Optionally, system 200 only determines a marking on the holder in order to correlate the position of the stone with respect to the determination of the external structure of the stone provided by apparatus 100 or the like. Alternatively, the stone is marked with laser signs and system 200 determines the location of the laser signs of the stone.

System 200 includes a controller for controlling the inspection process. Optionally, the controller of system 200 is controller 230 shown in FIG. 3 and matches between the external reference scanning of system 200 and the outline of the stone received from apparatus 100.

Optionally, during external reference scanning shown in FIG. 2A, the immersion medium is prepared as detailed in FIG. 6C above.

FIG. 2B depicts stone 202 fixed on a holder 204, which is mounted on a tube 296. The stone is positioned in compartment 280 in which foreign substances such as air and contaminants that may be present in air are to be removed from the stone. In an exemplary embodiment, the foreign substances are removed by applying vacuum and/or inert gas (606 in FIG. 6A) to compartment 280. When stone 202 is inserted into compartment 280, the compartment is sealed around tube 296 and a stream of inert gas, such as helium, is inserted through an opening 284. Optionally, opening 286 is provided for application of vacuum by evacuation of air. Alternatively, opening 284 may serve both for insertion of inert gas and for application of vacuum.

A port 282 is optionally provided to allow or block passage to the immersion medium in order to prevent contamination of container 222 by foreign substances present in compartment 280. Port 282 is shown in FIG. 2B as blocking the passage between compartment 280 and a compartment 222, which includes an immersion medium 220. After removing the foreign substances from compartment 280 and achieving a desired atmosphere, port 282 opens the passageway to allow tube 296 to be lowered into container 222 to dispose stone 204 in immersion medium 220, as shown in FIG. 2C. When port 282 is open, compartment 280 and container 222 are defined in a same sealed unit. At this stage, inert gas may be streamed through one or both openings 284 and 290.

Optionally, tube 296 is lowered to immerse the stone in the medium. Alternatively, cabin 228 is lifted. In an exemplary embodiment, the same imaging device or detector 212 and light source 206 are used for external reference scanning shown in FIG. 2A and internal scanning shown in FIG. 2C. According to this embodiment, cabin 228 is elevated to lift the immersion medium to the stone at the position of the detector 212 and light source 206. Alternatively, tube 296, detector 212 and source 206 are lowered to the location of the immersion medium.

Medium 220 is heated by a heater or heaters 287. Stone 202 is preferably heated before immersing in the heated medium. The stone may be heated while passing through port 282 which is heated by heaters 288.

Figure 3:
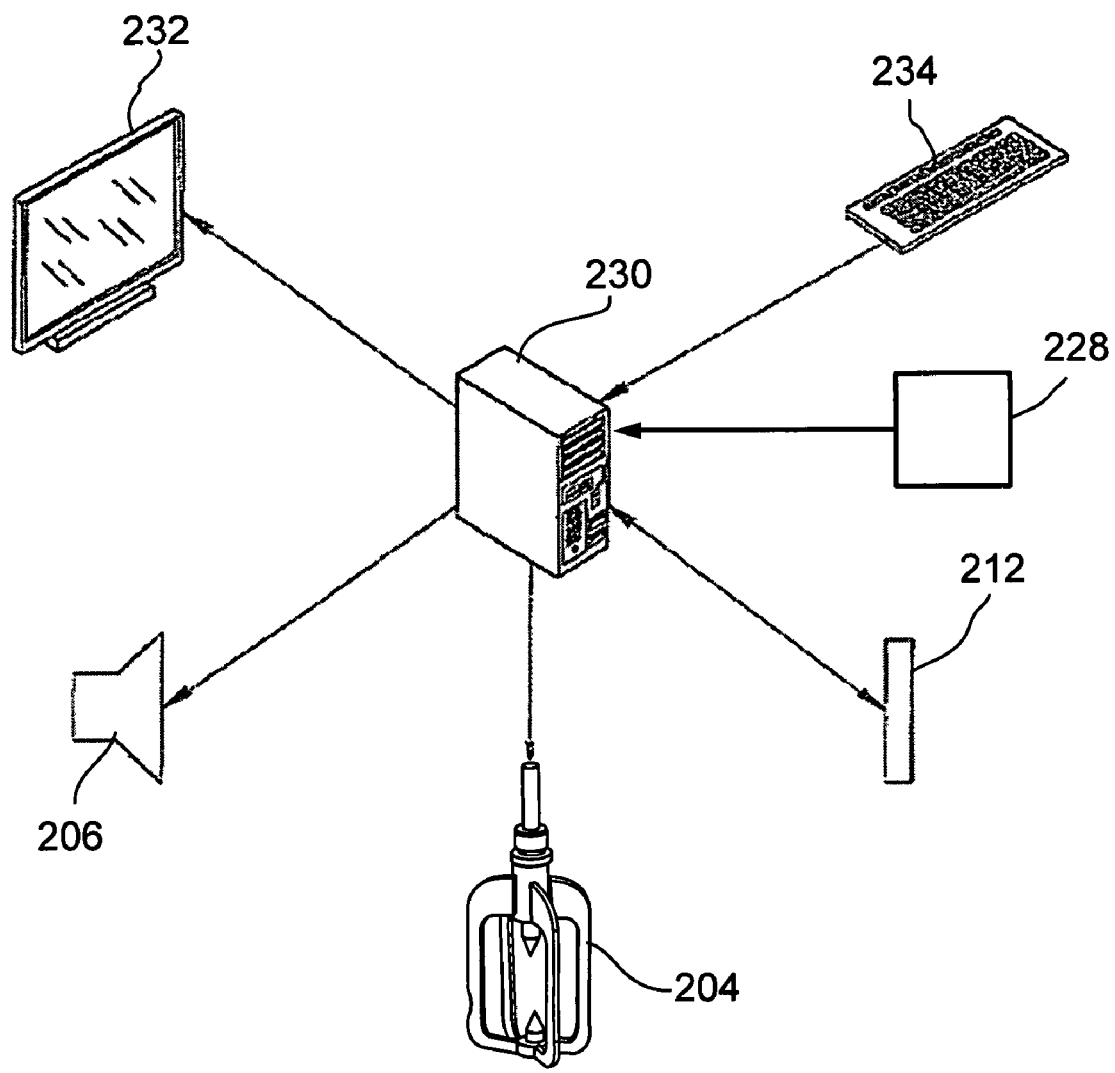
FIG. 3 is a schematic illustration of a controller and directions of primary signals with respect to the involved components of the apparatus of FIG. 2, in accordance with an exemplary embodiment of the invention.

Optionally, a motor (not shown) is connected to a spindle inside tube 296 for rotating stone 202 in container 222. The rotation may be controlled by a controller 230 (FIG. 3). Other means for rotation may be used, including rotation by hand. Optionally, a transducer (not shown) is provided for measuring the rotational position of the stone.

FIG. 2C shows immersion medium 220 as described above partially filling compartment 222 and covering the stone. The temperature of the medium and the wavelengths of the light are set so that the refraction index of the medium and the stone match as closely as practical, for example within a difference of refractive index between 0 and 0.5, preferably, less than 0.1. Optionally, the temperature is about 220° C., 235° C. or 240° C. and the wavelength is between 1.1 and 1.2 micron. Immersion at these conditions substantially eliminates the refractions and internal reflections in the stone and the multiple deflected images of inclusions. Light 208 entering the stone will largely pass through, but an inclusion 214 will absorb/reflect the light. The detector 212 is adapted to pass only the wavelength region substantially appropriate for the close refraction index. Thus, detector 212 detects and records the inclusion in its substantially true position 216 relative to a brighter background 218.

Optionally, light source 206 comprises a telecentric lens and/or a narrow band pass filter which is filtering the radiated light to be transmitted through the stone and the medium. Detector 212 is optionally a commercial camera, such as a digital camera. Optionally, a high resolution camera should be used to detect small inclusions in the stone, for example at least 1280*1024 pixels or more.

Note that the brightness of the shadow 218 formed by the stone correlates with the difference of absorption of the light in the medium and in the stone. This shadow may be used to reconstruct the external surface of the stone. In addition, since the absorption of light by the stone and the medium differs, a reference of the external surface of the stone can be received through detector 212 and used to reconstruct the external surface of the stone.

Responsive to control signals sent from a controller 230 (FIG. 3), holder 204 is rotated around an axis of tube 296 and a plurality of images of different orientations of the stone is detected and sent to the controller. These recorded projections are used to reconstruct the position of the inclusion with respect to the coordinates of apparatus 100. Known methods such as triangulation, back-projection, reverse Radon transform and others may be employed and optionally performed on controller 230, in order to construct the 3D geometry of the flaws from the series of 2D images. Optionally, methods known for tomographic imaging are used for construction of the 3D geometry. Optionally, controller 230 has an associated user interface including an input station 234, which may include a keyboard and/or mouse and/or a display 232 for displaying status and/or results of analysis of acquired data.

In an exemplary embodiment of the invention, the reconstruction of the position of the inclusion is based on one or more of the following feature:

1. The rotation axis is parallel to detector 212.
2. The rotation axis is stable during the whole procedure.
3. The rotation velocity is constant and known.
4. The detecting rate is constant.
5. Optionally, the optical magnification is known and the optics is telecentric.
6. The refractive index of the immersion medium is close to the refractive index of the stone, preferably within 0.1.

In an exemplary embodiment, the rotation velocity and detecting rate is not constant but the rotation is stopped and the stone is detected from two or more orientations thereof. In addition, the detecting rate is not necessarily constant, so long as the position for each image is known.

Optionally, the following method is used for reconstruction of the position of inclusions:

The center of rotation projection on the camera sensor is found, optionally by calculating the auto-correlation of one image with the mirrored image that was taken 180 degrees from the first. Optionally, in order to improve this calculation, the center is calculated for various pairs of images and an average of the center is then calculated.

In an exemplary embodiment standard tomographic reconstruction algorithms or triangulation are used to determine the positions of all the inclusions. Such reconstruction may also provide a reference outline of the gemstone.

At this point the inclusion appears in the sections as dark spots. These inclusions are located by means of threshold. The dark spots located may indicate, in addition to flaws inside the stone, bubbles adhered to the stone or filth in the medium. These are distinguished by comparing the result of the internal scanning process to the external structure of the stone received by apparatus 100. For example, dark spots appearing on or within the external structure of the stone will be indicated as a flaw in the stone. On the other hand, any spot that is located outside the external structure will be neglected as indicating a bubble or filth in the medium.

Since the coordinates of the outer contour are acquired in the same coordinate space as those of the inclusions (because the stone is kept in the same holder), the position of the inclusions can be mapped into the coordinates of the stone.

Optionally, one or more marks are made on the rough stone, by a laser or the like (not shown), while the gem is in the apparatus to allow for easier alignment of the stone during the realign operation. Alternatively or additionally, the stone is transferred to a marking station while still mounted on holder 204. Alternatively or additionally, the stone is transferred to a sawing station while still mounted on holder 204.

In some embodiments, the refraction index of the medium 220 may differ to a certain extent from that of the stone 202 for the irradiating light 208. Consequently the detector detects and records into controller 230 a certain deviation of the inclusions in the stone. In many cases, the deviation is relatively small and the reconstruction algorithm can compensate for the deviation.

Optionally detector 212 comprises a radiation sensitive solid-state device, or a matrix of photocells, or alternatively or additionally, a photographic film or other imaging device.

Figure 4:
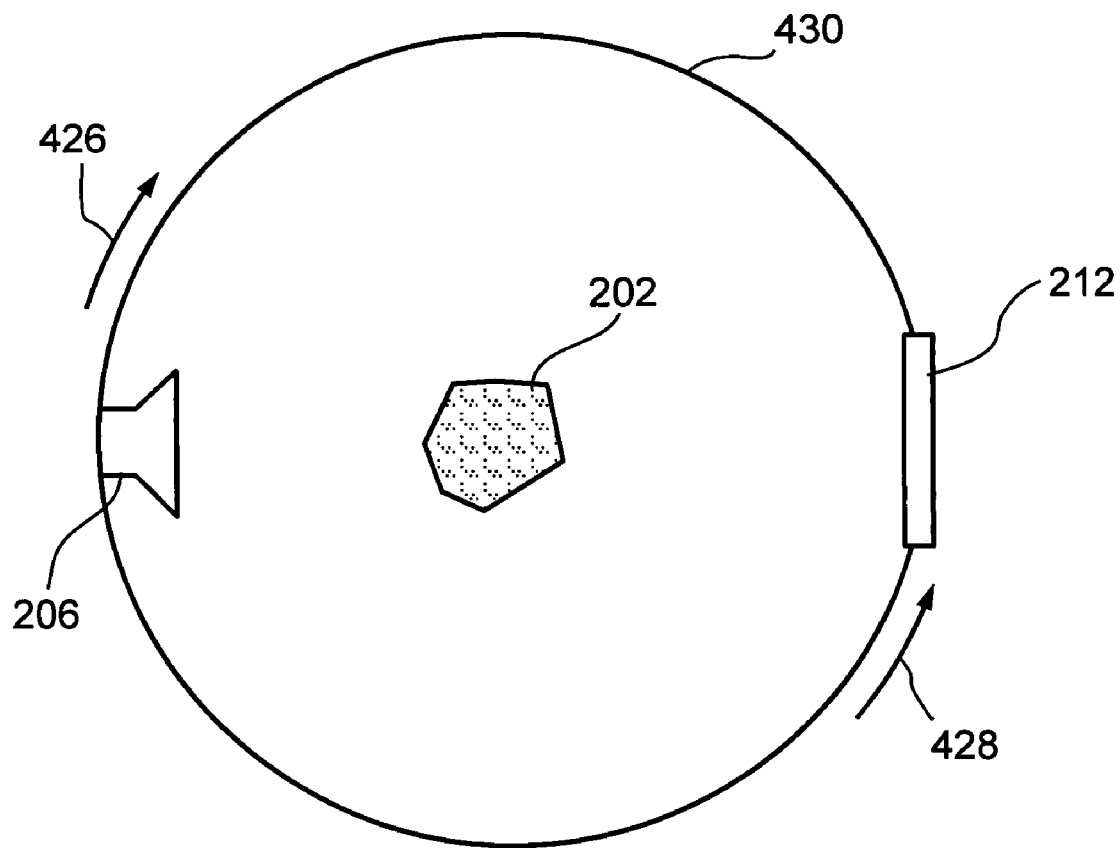
FIG. 4 is a schematic illustration of an alternative rotation of the imaging apparatus of FIGS. 2A-2C, in accordance with an exemplary embodiment of the invention.

Optionally, instead of rotating holder 204 with the gem, alternatively or additionally according to an exemplary embodiment, the holder and gem may be stationary and the detector, optionally with the light source, will rotate around them due to signals from controller 230, as shown schematically in FIG. 4. Here gem 202 is stationary and source 206 and detector 212 are rotating in unison in either direction 426 or 428. In this embodiment, container 430 preferably comprises a cylindrical transparent wall and detector 212 has a cylindrical lens to overcome the optical deformation of the light when passing through the high index cylindrical medium to air. Optionally, container 430 may be a sphere or any other shape.

Figure 5:
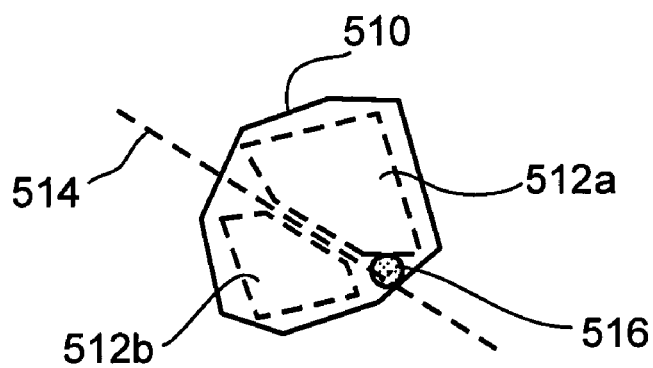
FIG. 5 is a schematic illustration of a rough stone with superimposed polished gems and an example of a dividing plane that eliminates an inclusion, in accordance with an exemplary embodiment of the invention.

Implemented in a program in controller 230, an exemplary embodiment of a method to determine the value of a gemstone with respect to its potential to produce polished gems responsive to the position and size of a flaw and to the internal stresses in the stone is described below, and partially depicted schematically in FIG. 5.

The program is provided with:

(a) A geometric model of the gemstone 510 and the inclusion 516 therein (for example, as disclosed above);

(b) Internal stresses in the stone. The internal stresses may be detected by tools of the art, such as a polarizer;

(c) The color of the stone. The color may be measured by tools of the art;

(d) Pre-defined scaleable geometrical models of polished gems (exemplified by 512a and 512b); and (e) A value functions of the stone. The value is a function of the "4C" (Clarity, Cut, Color and Carat).

Each of the latter polished models is associated with a value on a common scale, optionally taking into account its size, color and clarity. Optionally and additionally, flaw size, shade and position inside the gem, affect a gem value; optionally or additionally, other factors may count for value. Optionally and additionally, polishing costs and other cost related factors may be associated with the model on the same scale.

The controller program fits models of cut gems into the model of the uncut stone. Various fitting techniques in the art may be used such as linear or non-linear optimization, heuristic algorithms, genetic algorithms and others.

The controller program defines sawing planes (514) and a value of the cut stones dependent on its characteristics and whether the stone includes inclusions or not. The value of the cut stone will depend on the size, position and type of the inclusion. The controller can be programmed to either present various options to the user or to automatically define a best use of the stone, based on predetermined criteria. Generally these criteria are based on the highest overall value of the gemstones that can be manufactured from the rough stone.

Optionally the preferred goal is the largest flawless polished gems whereby the planes pass through an inclusion or isolating it.

Optionally the preferred goal is the highest value flawless polished gems such as better cut or shape at the expense of size whereby the planes go through an inclusion or isolating it.

Optionally the preferred goal is the highest value polished gems, some of which optionally including flaws, for example larger size or better cut at the expense of clarity.

Alternatively or additionally, the preferred goal is the best effectiveness of value to cost such as value less cost, in combination with any of the preferred values as disclosed above.

Optionally, the decision may be tuned to use a combination of criteria for preferred value goals.

Optionally or additionally, the controller reports a set of preferred planes according to the specified goal or goals. Alternatively or additionally, it reports a list of sets of planes ranked according to the preferred goal or goals.

Alternatively or additionally, for a set of such dividing planes the controller reports the value of potential resultant polished gems; optionally and additionally, it reports the cost involved in producing them; optionally and additionally, it reports a value of cost effectiveness such as the value after cost deduction.

Optionally or additionally, the report comprises the stone value, represented as the value of the potential polished gems, optionally or additionally with some cost compensation.

Optionally, the stone model and respective dividing planes are recorded, and optionally reported such that they can be read and construed for practical use.

Optionally, any of the output of the aforementioned exemplary embodiments, namely, the stone structure, inclusions positions therein or preferred cutting planes, may be input into a machinery; optionally it is a sawing equipment; alternatively or additionally, a polishing equipment; optionally the input is automatic.

FIG. 8 is a schematic illustration of a holder (dop or base) for fixing a stone in accordance with an exemplary embodiment of the invention. A holder 904 is shown which provides minimal interference with the scan of the stone. Holder 904 includes an upper cone 910 and a lower cone 912 for screwing the stone in place. Optionally, only upper cone 910 screws the stone into place and cone 912 provides support for the stone. The top part of upper cone 910 optionally comprises a shaft, adapted to be position in a tube 296 as shown in FIGS. 2A-C. Holder 904 further includes four wings 914 surrounding the stone. In the embodiment shown in FIG. 8, each two wings are parallel to each other thereby defining a single obstruction in the scan process. Alternatively, only two wings 914 are provided. Preferably, the wings have a small thickness in order to provide minimal obstruction to the scan process. Optionally, the wings have a thickness of about 0.5 mm.

Preferably, the wings are made of a material suitable for the immersion medium. For example, when selenium is used as the immersion medium, the wings are preferably made of steel which is resistant to corrosion by selenium. In addition, reflection of the material in the light should be taken into consideration. Preferably, the wings should be made of a non-flexible and rigid material in order to support the stone.

Optionally, one of wings 914 is marked by notch 916 for correlation of the position of the stone between external and internal scanning. The external reference scan provides the necessary position information, except for the position of rotation. Notch 296 can provide the necessary information for position measurement of rotation.

It is noted that the holder shown in FIG. 9 is not generally usable in cutting and polishing the stone, because of the obstructions of the wings.

It should be understood that while the invention is described above in the context of uncut diamonds, it is equally applicable to cut and polished diamonds.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb. The term "rough" as used in the claims to describe a gemstone is used to indicate a gemstone wherein at least part of the gemstone is uncut or unpolished.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

What is claimed is:

1. An apparatus for determining location of at least one inclusion in a gemstone having a first refractive index, comprising:

a container adapted for containing a material having a second refractive index;

a holder operative to support a gemstone in the container and in the material when the container contains the material;

an illuminator positioned and adapted to illuminate said gemstone when disposed within said material in said container, with illumination at which said gemstone and said material have their respective first and second index of refraction;

a detector that detects illumination from the illuminated gemstone and said material and produces signals responsive thereto;

a controller that receives the signals and is operative to determine a location of an inclusion in the gemstone based on the signals; and a system, operative to reduce the presence within said material, at least when the gemstone is disposed therein, of any substance other than inclusions, having a third refractive index.

2. An apparatus according to claim 1, wherein a difference between said first and second refractive indices is in the range between 0 and less than 0.5 and between the first and third refractive index is out of said range.

3. An apparatus according to claim 1, wherein a difference between said first and second refractive indices is in the range between 0 and 0.1 and between the first and third refractive index is out of said range.

4. An apparatus according to claim 1, wherein the apparatus contains means for changing the orientation of one or more of said gemstone, said detector or said illuminator such that the detector detects said light in more than one such orientation.

5. An apparatus according to claim 1, wherein the detector is an image detector.

6. An apparatus according to claim 1, wherein the detector, the gemstone and the illuminator are disposed on one optical axis so that the detector detects light transmitted by the gemstone.

7. An apparatus according to claim 6, wherein the gemstone is rotated around an axis which crosses said optical axis, such that signals representative of illumination incident on the gemstone from a plurality of directions, are produced by the detector and wherein the controller determines the position of inclusions based on such signals.

8. An apparatus according to claim 1, further comprising a heater for heating said material in solid form to become a liquid having said second refractive index, before said gemstone is disposed therein.

9. An apparatus according to claim 8, wherein said heater surrounds the container to provide uniform heating of said material therein.

10. An apparatus according to claim 8, further including means for controlling the uniformity of the temperature of the material at least along an optical axis of the illuminator and detector.

11. An apparatus according to claim 8, wherein the material in said solid form is in the form of pellets before said heating.

12. An apparatus according to claim 11, wherein said system includes a device for the withdrawal of gas bubbles from said material before said gemstone is introduced therein.

13. An apparatus according to claim 12, wherein said device is adapted for applying vacuum to the interior of said container.

14. An apparatus according to claim 12, wherein said system is adapted for applying vacuum before and/or during heating of the material.

15. An apparatus according to claim 1, wherein said system includes a source of an inert gas which is connected to the container so as to introduce said gas therein.

16. An apparatus according to claim 15, wherein said source of inert gas is adapted for introducing inert gas to the container before the material is heated.

17. An apparatus according to claim 15, wherein said source of inert gas is a source of helium.

18. An apparatus according to claim 1, wherein said container is sealable such that contaminants can not enter the container when it is sealed.

19. An apparatus according to claim 18, wherein the container comprises a port for introducing the gemstone into the container while keeping the container sealed.

20. An apparatus according to claim 19, wherein the port includes a passageway through which the gemstone passes on its path to the material, said passageway being heated so as to heat the gemstone to a temperature approximately that of the material.

21. An apparatus according to claim 1, further comprising means for moving said gemstone into said material at a speed which is slow enough to prevent the entrance of gas bubbles into said material.

22. An apparatus according to claim 1, wherein said holder comprises a mechanism that clamps the gemstone between two points on the gemstone.

23. An apparatus according to claim 22, wherein the two points are connected by a rigid structure.

24. An apparatus according to claim 1, further including reference means for establishing a reference system for said detecting when disposed within said material in said container, in a plurality of orientations thereof, said reference means constituting a part of said holder.

25. An apparatus according to claim 24, wherein said reference means comprises a scanner for scanning the external surface of said gemstone before its insertion in said material.

26. An apparatus according to claim 1, further including means for obtaining an outline of an external structure of the gemstone, wherein said controller is adapted to correlate between said outline and said signals to determine the position of said inclusion relative to said external structure.

27. An apparatus according to claim 26, wherein the means for obtaining is adapted to determine said outline of a gemstone having a coating thereon.

28. A system for determining location of inclusions in a gemstone having a first refractive index, comprising:
    an apparatus according to claim 1, adapted for performing the determination of said inclusions, under predetermined conditions; and
    a cleaning device for cleaning external surface of the gemstone, prior to its being introduced in said apparatus, from a medium other than possible inclusions, which either constitutes a substance having a third refractive index, whose difference from the first refractive index, when illuminated by said illumination, can cause artifacts, or is capable of producing such substance in interaction with said material or with the gemstone under said predetermined conditions.

29. A system according to claim 28, wherein said cleaning device comprises sonication means for aiding said cleaning.

30. A system according to claim 28, wherein said cleaning device and said apparatus are adapted for mounting therein of a same holder for holding said gemstone.

31. A system according to claim 29, wherein said cleaning device is adapted for mounting therein of a plurality of holders of the kind mountable in said apparatus.

32. A system according to claim 28, wherein said cleaning device comprises a container into which the gemstone is placed, the container containing a cleaning liquid capable of removing said medium from the external surface of the gemstone.

33. A system according to claim 31, wherein said cleaning device comprises a container into which the gemstone is placed, the container containing a cleaning liquid capable of removing said medium from the external surface of the gemstone and simultaneously cleaning a plurality of mounted gemstones.

34. A method for determining the position of inclusions in a gemstone, comprising:
    fixing the position of the gemstone in a holder;
    disposing a gemstone in the holder, having a first refractive index, in a material having a second refractive index;
    reducing the presence, within said material, of any substance, other than inclusion, having a third refractive index;
    detecting illumination of the gemstone; and
    determining a location of an inclusion based on said detection.

35. A method according to claim 34, wherein reducing the presence of any substance is performed before disposing the gemstone in the material.

36. A method according to claim 34, wherein reducing the presence of any substance comprises withdrawing gas bubbles from the material.

37. A method according to claim 34, wherein reducing the presence of any substance comprises applying a vacuum to a container in which the material is located.

38. A method according to claim 34, wherein reducing the presence of any substance comprises introducing inert gas into a container in which the material is located.

39. A method according to claim 38, wherein introducing inert gas comprises introducing helium.

40. A method according to claim 34, wherein the gemstone is clamped on a holder during said method.

41. A method according to claim 34, wherein a difference between said first and second refractive indices is in the range between 0 and less than 0.5.

42. A method according to claim 34, wherein a difference between said first and second refractive indices is in the range between 0 and 0.1.

43. A method according to claim 34, wherein detecting illumination of the gemstone comprises detecting from a plurality of orientations.

44. A method according to claim 34, further comprising: heating the material in solid form to become a liquid having said second refractive index, before disposing said gemstone in said material.

45. A method according to claim 44, wherein heating the material comprises changing the form of the material from pellets to liquid.

46. A method according to claim 34, wherein disposing the gemstone comprises disposing at a speed which is slow enough to prevent the entrance of bubbles of said inert gas into said material.

47. A method according to claim 34, further comprising: cleaning the gemstone from a medium other than possible inclusions, which either constitutes a substance having a third refractive index, different from the first and second refractive indices, or is capable of producing such substance in interaction with said material or with the gemstone during detection.

48. A method according to claim 47, wherein said cleaning the gemstone comprises cleaning by a cleaning liquid capable of removing said medium from the external surface of the gemstone.

49. A method according to claim 34, wherein detecting illumination comprises detecting near-infra-red illumination.

50. A method according to claim 49, wherein the illumination has a wavelength between 0.8 and 2 microns.

51. A method according to claim 34, further comprising:
obtaining a geometrical representation of the external surface of the gemstone relative to a respective coordinate system, wherein determining a location comprises
obtaining a geometrical representation of the inclusions in the gemstone relative to the same coordinate system.

52. A method according to claim 34 and including: evaluating the gemstone.

53. A method according to claim 52, wherein evaluating the gemstone includes determining one or more dividing planes for dividing the gemstone, based on the positions of the inclusions.

54. A method according to claim 52, wherein evaluating of the gemstone is responsive to a value of at least one potential polished gem yieldable by the gemstone.

55. A method according to claim 54, wherein the value of the potential polished gem is responsive to a size and geometry of a potential flawless polished gem.

56. A method according to claim 34, wherein the material comprises a chalcogenide element in group 16 of the periodic table.

57. A method according to claim 34, wherein the material comprises selenium.

58. A method according to claim 34, wherein the material comprises elemental selenium.

59. A method according to claim 34, wherein the material comprises thallium iodide.

60. A method according to claim 34, wherein the material comprises thallium bromide.

61. A method according to claim 34, wherein the material comprises a molten material.

62. A method according to claim 34, wherein the material comprises one or more of antimony pentasulfide, antimony triiodide, antimony trisulfide, arsenic, arsenic disulfide, arsenic selenide, arsenic tribromide, arsenic triiodide, arsenic trisulfide, arsenous acid, chloro-chromic acid, chromic acid, cyanogen iodide, lead chromate, mercuric iodide, phosphorus, selenium, elemental selenium, selenium tetrachloride, selenium arsenic, bromine, iodine, silver bromide, silver chloride, silver iodide, sulfur, tellurium, tellurium chloride, thallium iodide-bromide, thallium monobromide, thallium monochloride, thallium monoiodide, stannic iodide, arsenic trichloride, piperine, boracic acid and lead chromate.

63. A method according to claim 34, wherein the material and the gemstone are at a temperature of between 220 and 500 degrees Celsius.

64. A method according to claim 34, wherein the material and the gemstone are at a temperature of between room temperature and 250 degrees Celsius.

65. A method according to claim 34, wherein the gemstone is a diamond.

66. A method according to claim 34, wherein the gemstone is rough.

67. A method according to claim 34 wherein the gemstone is polished.

68. An apparatus for evaluating of a gemstone, comprising:
an optical device adapted to scan the external surface of a gemstone;
a controller adapted to correlate the external scan of the optical device with an accurate outline of said gemstone;
a container adapted to include said stone and material having a refractive index within 0.1 of that of said gemstone;
a light source adapted to introduce light having a wavelength matching the temperature and refractive index of said material and light; and
a detector adapted to detect light passing through said gemstone.

69. A system for evaluating a gemstone, the system comprising:
means for producing an accurate outline of an external structure of a gemstone;
means for scanning the external surface of said gemstone;
means for detecting inclusions in said gemstone; and
means for correlating between said outline, said external scan and said inclusions.

* * * * *